US012662685B2

(12) United States Patent
Jensen et al.

(10) Patent No.: US 12,662,685 B2
(45) Date of Patent: Jun. 23, 2026

(54) SELF-INACTIVATING TRANSPOSASE PLASMIDS AND USES THEREOF

(71) Applicant: Seattle Children's Hospital, Seattle, WA (US)

(72) Inventors: Michael C. Jensen, Seattle, WA (US); Joshua Gustafson, Seattle, WA (US); Joseph Cheng, Seattle, WA (US); Rachel Wilson, Seattle, WA (US); Kamila Sabina Gwiazda, Seattle, WA (US); Jeremy Bjelajac, Seattle, WA (US)

(73) Assignee: Seattle Children's Hospital, Seattle, WA (US)

( * ) Notice: Subject to any disclaimer, the term of this patent is extended or adjusted under 35 U.S.C. 154(b) by 1128 days.

(21) Appl. No.: 17/271,814

(22) PCT Filed: Aug. 28, 2019

(86) PCT No.: PCT/US2019/048663
§ 371 (c)(1),
(2) Date: Feb. 26, 2021

(87) PCT Pub. No.: WO2020/047165
PCT Pub. Date: Mar. 5, 2020

(65) Prior Publication Data
US 2021/0324407 A1       Oct. 21, 2021

Related U.S. Application Data

(60) Provisional application No. 62/724,236, filed on Aug. 28, 2019.

(51) Int. Cl.
*C12N 15/85*        (2006.01)

(52) U.S. Cl.
CPC .......... *C12N 15/85* (2013.01); *C12N 2800/90* (2013.01)

(58) Field of Classification Search
CPC ..... C12N 15/85; C12N 2800/90; C12N 15/90
See application file for complete search history.

(56) References Cited

U.S. PATENT DOCUMENTS

| | | | |
|---|---|---|---|
| 2010/0240133 A1* | 9/2010 | Brivanlou | C12N 15/90 435/465 |
| 2010/0287633 A1 | 11/2010 | Ostertag et al. | |
| 2017/0159070 A1 | 6/2017 | Wu | |

FOREIGN PATENT DOCUMENTS

| | | | | |
|---|---|---|---|---|
| WO | WO 95/23875 | 9/1995 | | |
| WO | WO-2015157579 A2 * | 10/2015 | | A61K 31/00 |
| WO | WO 2017/054647 A1 | 4/2017 | | |

OTHER PUBLICATIONS

Zhang et al. Distributions of Transposable Elements Reveal Hazardous Zones in Mammalian Introns. PLoS Comput Biol. May 2011;7(5):e1002046 (Year: 2011).*
Boualle gue et al. Molecular Evolution of piggyBac Superfamily: From Selfishness to Domestication. Genome Biol Evol. Feb. 1, 2017;9(2):323-339. (Year: 2017).*
Wakabayashi-It et al. Characterization of the Regulatory Elements in the Promoteorf the Human Elongation Factor-la Gene. J Biol Chem. Nov. 25, 1994;269(47):29831-7. (Year: 1994).*
Cracking the Code of life. Nova Online (accessed at: https://www.pbs.org/wgbh/nova/genome/expl_05_introns.html) (Year: 2001).*
Derived. Dictionary.Com (accessed at: https://www.dictionary.com/browse/derived) (Year: 2024).*
Chakraborty, Syandan et al., "Vector modifications to eliminate transposase expression following piggyBac-mediated transgenesis" Scientific Reports, Dec. 2014, pp. 1-9, vol. 4, No. 7403.
International Search Report for PCT/US2019/048663 dated Jan. 6, 2020.
Brown et al., Apr. 1989, Retroviral integration: struciure of the initial covalent product and its precursor, and a role for the viral IN protein, Proc. Natl. Acad. Sci. USA, 86:2525-2529
Colegio et al., Apr. 2001, In vitro transposition system for efficient generation of random mutants of campylobacter jejuni, J. Bacteriol., 183(7):2384-2388.
Devine et al., 1994, Efficient integration of artificial transposons into plasmid targets in vitro: a useful tool for DNA mapping, sequencing and genetic analysis, Nucleic Acids Res., 22(18):3765-3772.
Ichikawa et al., Nov. 5, 1990, In vitro transposition of transposon Tn3*, J. Biol. Chem., 265(31):18829-18832.
Kirby et al., 2002, Cryptic plasmids of *Mycobacterium avium*: Tn552 to the rescue, Mol. Microbiol., 43(1):173-186.
Lampe et al., 1995, The phage Mu transpososome core: DNA requirements for assembly and function, EMBO J., 15:5470-5479.
Lemaigre et al., "Transcriptional control of genes that regulate glycolysis and gluconeogenesis in adult liver," Biochem. J. (1994) 303:1-14.
Loeken, 1993, Effects of mutation of the CREB binding site of the somatostatin promoter on cyclic AMP responsiveness in CV-1 cells, Gene Expr. 3(3):253-264.
McGehee et al., Apr. 1993, Differentiation-specific element: a cis-acting developmental switch required for the sustained transcriptional expression of the angiotensinogen gene during hormonal-induced differentiation of 3T3-L1 fibroblasts to adipocytes, Mol. Endocrinol. 7(4):551-560.
Ohtsubo et al., 1996, Bacterial insertion sequences, Curr. Top. Microbiol. Immunol. 204:1-26.
O'Reilly et al., Oct. 5, 1992, Identification of an activating transcription factor (ATF) binding site in the human transforming growth factor-beta 2 promoter, J. Biol. Chem. 267:19938-19943.
Sambrook et al., 1989, Molecular Cloning, A Laboratory Manual, Cold Springs Harbor Press, Cold Springs Harbor, NY (T)C).

(Continued)

*Primary Examiner* — Valarie E Bertoglio
*Assistant Examiner* — Briana N Ebbinghaus
(74) *Attorney, Agent, or Firm* — Knobbe, Martens, Olson & Bear, LLP

(57) ABSTRACT

Some embodiments provided herein relate to gene delivery systems and methods using a single plasmid that carries a self-inactivating transposase gene and a corresponding transposon. Some embodiments include nucleic acids having certain sequences, vector including such nucleic acids, and compositions including the vectors.

15 Claims, 15 Drawing Sheets

Specification includes a Sequence Listing.

(56)  References Cited

OTHER PUBLICATIONS

Singleton et al., 1994, Dictionary of Microbiology and Molecular Biology 2nd ed., J. Wiley & Sons, New York, NY (cover page).

Treisman, Feb. 1, 1990, The SRE: a growth factor responsive transcriptional regulator. (PMID:2133110), Seminars in Cancer Biology, 1(1):47-58.

Watson et al., eds., 1987, Molecular Biology of the Gene, 4th ed., The Benjamin/Cummings Publishing Company, Inc. (TOC).

Wilson et al., Dec. 2007, New transposon delivery plasmids for insertional mutagenesis in bacillus anthracis, J. Microbiol. Methods 71(3):332-335.

Ye et al., Oct. 14, 1994, Characterization of a silencer regulatory element in the human interferon-gamma promoter, J. Biol. Chem., 269:25728-25734.

Zhang et al., Oct. 2009, A novel mechanism of transposon-mediated gene activation, PLoS Genet. 5(10):e1000689.

* cited by examiner

SEQUENCE LISTING

<160> NUMBER OF SEQ ID NOS: 20

<210> SEQ ID NO 1
<211> LENGTH: 1140
<212> TYPE: DNA
<213> ORGANISM: Artificial Sequence
<220> FEATURE:
<223> OTHER INFORMATION: TRANSPOSASE REGION PIGGYBAC TRANSPOSASE 5 PRIME
      CATALYTIC REGION

<400> SEQUENCE: 1
atgggcagca gcctggacga cgagcacatc ctgtctgccc tgctgcaatc cgacgatgag       60
ctcgtgggcg aggacagcga cagcgagatc agcgatcacg tgtccgagga cgacgtgcag      120
tccgacaccg aggaagcctt catcgacgag gtgcacgaag tgcagcctac cagcagcggc      180

```
tccgagatcc tggacgagca gaacgtgatc gagcagcccg gaagctccct ggccagcaac    240
agaatcctga ccctgcccca gcggaccatc cggggcaaga acaagcactg ctggtccacc    300
agcaagagca cccggcggtc cagagtgtcc gccctgaata tcgtgcggag ccagaggggc    360
cccacccgga tgtgcagaaa catctacgac cccctgctgt gcttcaagct gttcttcacc    420
gacgagatca tctctgagat cgtgaagtgg accaacgccg agatctccct gaagcggcgc    480
gagtctatga ccggcgccac cttcagagac accaacgagg acgagatcta cgccttcttc    540
ggcatcctcg tgatgaccgc cgtgcggaag gacaaccaca tgagcaccga cgacctgttc    600
gaccggtccc tgagcatggt gtacgtgtcc gtgatgagcc gggacagatt cgacttcctg    660
atccggtgcc tgcggatgga cgacaagagc atcagaccca ccctgcgcga gaacgacgtg    720
ttcacccctg tgcggaagat ctgggacctg ttcatccacc agtgcatcca gaactacacc    780
cctggcgccc acctgaccat cgacgaacag ctgctgggct tcagaggccg gtgccccttc    840
agaatgtaca tccccaacaa gccctctaag tacggcatca agatcctgat gatgtgcgac    900
agcggcacca agtacatgat caacggcatg ccctacctgg gcagaggcac ccagacaaat    960
ggcgtgccac tgggcgagta ctacgtgaaa gaactgagca agcctgtgca cggctcctgc   1020
cggaacatca cctgtgacaa ctggttcacc tccatccccc tggccaagaa tctgctgcag   1080
gaaccctaca agctgacaat cgtgggcacc gtgcggtcca acaagcgcga gattcccgag   1140
```

```
<210> SEQ ID NO 2
<211> LENGTH: 939
<212> TYPE: DNA
<213> ORGANISM: Artifical Sequence
<220> FEATURE:
<223> OTHER INFORMATION: EF1a INTRON

<400> SEQUENCE: 2
```

```
gtaagtgccg tgtgtggttc ccgcgggcct ggcctcttta cgggttatgg cccttgcgtg     60
ccttgaatta cttccacgcc cctggctgca gtacgtgatt cttgatcccg agcttcgggt    120
tggaagtggg tgggagagtt cgaggccttg cgcttaagga gccccttcgc ctcgtgcttg    180
agttgaggcc tggcttgggc gctgggccg ccgcgtgcga atctggtggc accttcgcgc     240
ctgtctcgct gctttcgata agtctctagc catttaaaat ttttgatgac ctgctgcgac    300 gcttttttc tggcaagata gtcttgtaaa tgcgggccaa gatctgcaca ctggtatttc     360
ggtttttggg gccgcgggcg cgacggggc ccgtgcgtcc cagcgcacat gttcggcgag     420
gcggggcctg cgagcgcggc caccgagaat cggacggggg tagtctcaag ctggccggcc    480
tgctctggtg cctggcctcg cgccgccgtg tatcgccccg ccctgggcgg caaggctggc    540
ccggtcggca ccagttgcgt gagcggaaag atggccgctt cccggccctg ctgcagggag    600
ctcaaaatgg aggacgcggc gctcgggaga gcgggcgggt gagtcaccca cacaaaggaa    660
aagggccttt ccgtcctcag ccgtcgcttc atgtgactcc acggagtacc gggcgccgtc    720
caggcacctc gattagttcg cttttggagt acgtcgtctt taggttgggg ggaggggttt    780
tatgcgatgg agtttcccca cactgagtgg gtggagactg aagttaggcc agcttggcac    840
ttgatgtaat tctccttgga atttgccctt tttgagtttg gatcttggtt cattctcaag    900
cctcagacag tggttcaaag ttttttttctt ccatttcag                           939
```

```
<210> SEQ ID NO 3
<211> LENGTH: 645
<212> TYPE: DNA
<213> ORGANISM: Artificial Sequence
```

```
<220> FEATURE:
<223> OTHER INFORMATION: PIGGYBAC TRANSPOSASE 5 PRIME CATALYTIC
      REGION+STOP CODON

<400> SEQUENCE: 3
gtgctgaaga actcccggtc cagacctgtg ggcaccagca tgttctgctt cgacggccct      60
ctgaccctgg tgtcctacaa gcccaagccc gccaagatgg tgtacctgct gagcagctgt     120
gacgaggacg ccagcatcaa cgagagcacc ggcaagcccc agatggtcat gtactacaac     180
cagaccaagg gcggcgtgga caccctggac cagatgtgca gcgtgatgac atgcagcaga     240
aagaccaacc ggtggcccat ggccctgctg tacggcatga tcaatatcgc ctgcatcaac     300
agcttcatca tctactccca caacgtgtcc agcaagggcg agaaggtgca gagccggaag     360
aaattcatgc ggaacctgta catgagcctg acctccagct tcatgagaaa gcggctggaa     420
gcccccaccc tgaagagata cctgcgggac aacatccagc acatcctgcc caacgaggtg     480
cccggcacca gcgacgatag cacagaggaa cccgtgatga agaagcggac ctactgcacc     540
tactgtccct ctaaaatccg gcggaaggcc aacgccagct gcaaaaagtg caagaaagtg     600
atctgccgcg agcacaacat cgatatgtgc cagagctgct tctga                     645

<210> SEQ ID NO 4
<211> LENGTH: 134
<212> TYPE: DNA
<213> ORGANISM: Artificial Sequence
<220> FEATURE:
<223> OTHER INFORMATION: SV40 LATE POLY(A)

<400> SEQUENCE: 4
gctttatttg tgaaatttgt gatgctattg ctttatttgt aaccattata agctgcaata      60
aacaagttaa caacaacaat tgcattcatt ttatgtttca ggttcagggg gagatgtggg     120 aggttttttta aagc                                                       134

<210> SEQ ID NO 5
<211> LENGTH: 242
<212> TYPE: DNA
<213> ORGANISM: Artificial Sequence
<220> FEATURE:
<223> OTHER INFORMATION: TRANSPOSON REGION 5 PRIME TERMINAL REPEAT

<400> SEQUENCE: 5
ttaaccctag aaagataatc atattgtgac gtacgttaaa gataatcatg cgtaaaattg      60
acgcatgtgt tttatcggtc tgtatatcga ggtttattta ttaatttgaa tagatattaa     120
gttttattat atttacactt acatactaat aataaattca acaaacaatt tatttatgtt     180 tatttatttta ttaaaaaaaa acaaaaactc aaaatttctt ctataaagta acaaaacttt     240
ta                                                                      242

<210> SEQ ID NO 6
<211> LENGTH: 241
<212> TYPE: DNA
<213> ORGANISM: Artificial Sequence
<220> FEATURE:
<223> OTHER INFORMATION: CORE/INSULATOR

<400> SEQUENCE: 6
gagggacagc ccccccccaa agcccccagg gatgtaatta cgtccctccc ccgctagggg      60
gcagcagcga gccgcccggg gctccgctcc ggtccggcgc tccccccgca tccccgagcc     120
ggcagcgtgc ggggacagcc cgggcacggg gaaggtggca cgggatcgct ttcctctgaa     180
```

```
cgcttctcgc tgctctttga gcctgcagac acctgggggg atacggggaa aaggctcgcg      240
a                                                                        241

<210> SEQ ID NO 7
<211> LENGTH: 245
<212> TYPE: DNA
<213> ORGANISM: Artificial Sequence
<220> FEATURE:
<223> OTHER INFORMATION: EF1a PROMOTER

<400> SEQUENCE: 7
ggatctgcga tcgctccggt gcccgtcagt gggcagagcg cacatcgccc acagtccccg       60
agaagttggg gggaggggtc ggcaattgaa ccggtgccta gagaaggtgg cgcggggtaa      120
actgggaaag tgatgtcgtg tactggctcc gcctttttcc cgagggtggg ggagaaccgt      180
atataagtgc agtagtcgcc gtgaacgttc tttttcgcaa cgggtttgcc gccagaacac      240
agctg                                                                   245

<210> SEQ ID NO 8
<211> LENGTH: 678
<212> TYPE: DNA
<213> ORGANISM: Artificial Sequence
<220> FEATURE:
<223> OTHER INFORMATION: eGFP Flanked by enzymatic cut sites NheI and
      BamHI

<400> SEQUENCE: 8
gctagcatgc ccgccatgaa gatcgagtgc cgcatcaccg gcaccctgaa cggcgtggag       60
ttcgagctgg tgggcggcgg agagggcacc cccgagcagg gccgcatgac caacaagatg      120
aagagcacca aggcgccct gaccttcagc ccctacctgc tgagccacgt gatgggctac       180
ggcttctacc acttcggcac ctaccccagc ggctacgaga accccttcct gcacgccatc      240
aacaacggcg gctacaccaa caccgcatc gagaagtacg aggacggcgg cgtgctgcac       300
gtgagcttca gctaccgcta cgaggccggc cgcgtgatcg gcgacttcaa ggtggtgggc      360
accggcttcc ccgaggacag cgtgatcttc accgacaaga tcatccgcag caacgccacc      420
gtggagcacc tgcaccccat gggcgataac gtgctggtgg gcagcttcgc ccgcaccttc      480
agcctgcgcg acggcggcta ctacagcttc gtggtggaca gccacatgca cttcaagagc      540
gccatccacc ccagcatcct gcagaacggg ggccccatgt cgccttccg ccgcgtggag      600 gagctgcaca gcaacaccga gctgggcatc gtggagtacc agcacgcctt caagacccc      660 atcgccttcg ccggatcc                                                     678

<210> SEQ ID NO 9
<211> LENGTH: 66
<212> TYPE: DNA
<213> ORGANISM: Artificial Sequence
<220> FEATURE:
<223> OTHER INFORMATION: T2A with AGG tag

<400> SEQUENCE: 9
ggcggcggag agggcagagg aagtcttcta acatgcggtg acgtggagga gaatcccggc       60
cctagg                                                                   66

<210> SEQ ID NO 10
<211> LENGTH: 578
<212> TYPE: DNA
<213> ORGANISM: Artificial Sequence
```

```
<220> FEATURE:
<223> OTHER INFORMATION: DHFRdm+STOP CODON Followed by enzymatic cut
      sites Acc65I and Not I

<400> SEQUENCE: 10
atggttggtt cgctaaactg catcgtcgct gtgtcccaga acatgggcat cggcaagaac      60
ggggacttcc cctggccacc gctcaggaat gaatccagat atttccagag aatgaccaca     120
acctcttcag tagaaggtaa acagaatctg gtgattatgg gtaagaagac ctggttctcc     180
attcctgaga agaatcgacc tttaaagggt agaattaatt tagttctcag cagagaactc     240
aaggaacctc cacaaggagc tcattttctt tccagaagtc tagatgatgc cttaaaactt     300
actgaacaac cagaattagc aaataaagta gacatggtct ggatagttgg tggcagttct     360
gtttataagg aagccatgaa tcacccaggc catcttaaac tatttgtgac aaggatcatg     420
caagactttg aaagtgacac gttttttcca gaaattgatt tggagaaata taaacttctg     480
ccagaatacc caggtgttct ctctgatgtc caggaggaga aaggcattaa gtacaaattt     540
gaagtatatg agaagaatga ttaaggtacc gcggccgc                             578

<210> SEQ ID NO 11
<211> LENGTH: 135
<212> TYPE: DNA
<213> ORGANISM: Artificial Sequence
<220> FEATURE:
<223> OTHER INFORMATION: RBG/POLY(A)

<400> SEQUENCE: 11
ttttccctct gccaaaaatt atggggacat catgaagccc cttgagcatc tgacttctgg      60
ctaataaagg aaatttattt tcattgcaat agtgtgttgg aattttttgt gtctctcact     120
cggaaggaca taagg                                                      135

<210> SEQ ID NO 12
<211> LENGTH: 243
<212> TYPE: DNA
<213> ORGANISM: Artificial Sequence
<220> FEATURE:
<223> OTHER INFORMATION: CORE/INSULATOR

<400> SEQUENCE: 12
atggctagat ctttttcccc gtatcccccc aggtgtctgc aggctcaaag agcagcgaga      60
agcgttcaga ggaaagcgat cccgtgccac cttccccgtg cccgggctgt ccccgcacgc     120
tgccggctcg gggatgcggg gggagcgccg gaccggagcg gagccccggg cggctcgctg     180 ctgccccocta gcgggggagg gacgtaatta catccctggg ggctttgggg gggggctgtc     240
cct                                                                   243

<210> SEQ ID NO 13
<211> LENGTH: 313
<212> TYPE: DNA
<213> ORGANISM: Artificial Sequence
<220> FEATURE:
<223> OTHER INFORMATION: 3 PRIME TERMINAL REPEAT

<400> SEQUENCE: 13
gatatctata acaagaaaat atatatataa taagttatca cgtaagtaga acatgaaata      60
acaatataat tatcgtatga gttaaatctt aaaagtcacg taaaagataa tcatgcgtca     120
ttttgactca cgcggtcgtt atagttcaaa atcagtgaca cttaccgcat tgacaagcac     180
gcctcacggg agctccaagc ggcgactgag atgtcctaaa tgcacagcga cggattcgcg     240
```
ctatttagaa agagagagca atatttcaag aatgcatgcg tcaattttac gcagactatc          300
tttctagggt taa                                                             313

<210> SEQ ID NO 14
<211> LENGTH: 43
<212> TYPE: DNA
<213> ORGANISM: Artificial Sequence
<220> FEATURE:
<223> OTHER INFORMATION: 3 PRIME TERMINAL REPEATNANOPLASMID BACKBONE
      TRPA TERMINATOR Preceded by enzymatic cut site
      SalI

<400> SEQUENCE: 14
gtcgacccgc ctaatgagcc gcctaatgag cgggcttttt ttt                            43

<210> SEQ ID NO 15
<211> LENGTH: 281
<212> TYPE: DNA
<213> ORGANISM: Artificial Sequence
<220> FEATURE:
<223> OTHER INFORMATION: R6K MINI ORIGIN

<400> SEQUENCE: 15
ggcttgttgt ccacaaccgt taaaccttaa aagctttaaa agccttatat attctttttt          60
ttcttataaa acttaaaacc ttagaggcta tttaagttgc tgattatat taattttatt          120 gttcaaacat gagagcttag tacgtgaaac atgagagctt agtacgttag ccatgagagc          180
ttagtacgtt agccatgagg gtttagttcg ttaaacatga gagcttagta cgttaaacat          240
gagagcttag tacgtactat caacaggttg aactgctgat c                             281

<210> SEQ ID NO 16
<211> LENGTH: 150
<212> TYPE: DNA
<213> ORGANISM: Artificial Sequence
<220> FEATURE:
<223> OTHER INFORMATION: RNA-OUT

<400> SEQUENCE: 16
cacgttgtgg tagaattggt aaagagagtc gtgtaaaata tcgagttcgc acatcttgtt          60
gtctgattat tgattttttgg cgaaaccatt tgatcatatg acaagatgtg tatctacctt        120
aacttaatga ttttgataaa aatcattagg                                          150

<210> SEQ ID NO 17
<211> LENGTH: 467
<212> TYPE: DNA
<213> ORGANISM: Artificial Sequence
<220> FEATURE:
<223> OTHER INFORMATION: CMV-ENHANCER

<400> SEQUENCE: 17
ctagttatta atagtaatca attacggggt cattagttca tagcccatat atggagttcc          60
gcgttacata acttacggta aatggcccgc ctggctgacc gcccaacgac ccccgcccat          120
tgacgtcaat aatgacgtat gttcccatag taacgccaat agggactttc cattgacgtc          180
aatgggtgga gtatttacgg taaactgccc acttggcagt acatcaagtg tatcatatgc         240
caagtacgcc ccctattgac gtcaatgacg gtaaatggcc cgcctggcat tatgcccagt        300
acatgacctt atgggacttt cctacttggc agtacatcta cgtattagtc atcgctatta        360
ccatggtgat gcggttttgg cagtacatca atgggcgtgg atagcggttt gactcacggg        420

-continued

```
gatttccaag tctccacccc attgacgtca atgggagttt gttttgg              467

<210> SEQ ID NO 18
<211> LENGTH: 163
<212> TYPE: DNA
<213> ORGANISM: Artificial Sequence
<220> FEATURE:
<223> OTHER INFORMATION: CMV-CORE PROMOTER

<400> SEQUENCE: 18
caccaaaatc aacgggactt tccaaaatgt cgtaacaact ccgccccatt gacgcaaatg    60
ggcggtaggc gtgtacggtg ggaggtctat ataagcagag ctcgtttagt gaaccgtcag   120
atcgcctgga gacgccatcc acgctgtttt gacctccata gaa                     163

<210> SEQ ID NO 19
<211> LENGTH: 993
<212> TYPE: DNA
<213> ORGANISM: Artificial Sequence
<220> FEATURE:
<223> OTHER INFORMATION: SUICIDE GENE SR39TK

<400> SEQUENCE: 19
atgcccacgc tactgcgggt ttatatagac ggtccccacg ggatggggaa aaccaccacc    60
acgcaactgc tggtggccct gggttcgcgc gacgatatcg tctacgtacc cgagccgatg   120
acttactggc gggtgctggg ggcttccgag acaatcgcga acatctacac cacacaacac   180
cgcctcgacc agggtgagat atcggccggg gacgcggcgg tggtaatgac aagcgcccag   240
ataacaatgg gcatgcctta tgccgtgacc gacgccgttc tggctcctca tatcggggggg   300 gaggctggga gctcacatgc cccgcccccg gccctcacca tcttcctcga ccgccatccc    360
atcgccttca tgctgtgcta cccggccgcg cggtacctta tgggcagcat gacccccccag   420 gccgtgctgg cgttcgtggc cctcatcccg ccgaccttgc ccggcaccaa catcgtgctt   480
ggggcccttc cggaggacag acacatcgac cgcctggcca aacgccagcg ccccggcgag   540
cggctggacc tggctatgct ggctgcgatt cgccgcgttt acgggctact tgccaatacg    600
gtgcggtatc tgcagtgcgg cgggtcgtgg cgggaggact ggggacagct ttcggggacg   660
gccgtgccgc cccagggtgc cgagcccag agcaacgcgg gcccacgacc ccatatcgggg    720 gacacgttat ttaccctgtt tcgggccccc gagttgctgg cccccaacgg cgacctgtat   780
aacgtgtttg cctgggcctt ggacgtcttg gccaaacgcc tccgttccat gcacgtcttt   840
atcctggatt acgaccaatc gcccgccggc tgccgggacg ccctgctgca acttacctcc   900
gggatggtcc agacccacgt caccacccccc ggctccatac cgacgatatg cgacctggcg    960
cgcacgtttg cccgggagat gggggaggct aac                                993

<210> SEQ ID NO 20
<211> LENGTH: 63
<212> TYPE: DNA
<213> ORGANISM: Artificial Sequence
<220> FEATURE:
<223> OTHER INFORMATION: T2A

<400> SEQUENCE: 20
ggcggcggag agggcagagg aagtcttcta acatgcggtg acgtggagga gaatcccggc    60
cct                                                                  63
```

SELF-INACTIVATING TRANSPOSASE PLASMIDS AND USES THEREOF

RELATED APPLICATIONS

This application is a U.S. National Phase Application of PCT International Application Number PCT/US2019/048663, filed on Aug. 28, 2019, designating the United States of America and published in the English language, which is an International Application of and claims the benefit of priority to U.S. Provisional Application No. 62/724,236, filed on Aug. 29, 2018. The disclosures of the above-referenced applications are hereby expressly incorporated by reference in their entireties.

REFERENCE TO SEQUENCE LISTING

The present application is being filed along with an Electronic Sequence Listing as an ASCII text file via EFS-Web. The Electronic Sequence Listing is provided as a file entitled SeqList-SCRI-198NP, created and last saved on Feb. 25, 2021, which is 13 KB in size. The information in the Electronic Sequence Listing is incorporated herein by reference in its entirety.

FIELD

Some embodiments provided herein relate to gene delivery systems and methods using a single plasmid that carries a self-inactivating transposase gene and a corresponding transposon. Some embodiments include nucleic acids having certain sequences, vector including such nucleic acids, and compositions including the vectors.

BACKGROUND

Transposon and transposase systems are useful for genetic engineering of cells as they efficiently insert foreign genetic material into cells of interest. Typically, this is done by delivering the transposon and transposase separately, due to safety reasons involving potential integrations of transposase genes into a host cell. Accordingly, current approaches for genetic delivery using a transposon or transposase requires a two-component system, which increases cost and complexity while decreasing efficiency. The need for new transposon and/or transposase systems that overcome the two-component requirement is manifest.

SUMMARY

Described herein are compositions, systems, and methods for genetic engineering of cells using a single plasmid that carries a self-inactivating transposase gene and a corresponding transposon, thereby providing a highly efficient single-component transposon/transposase system.

Some embodiments provided herein relate to a vector for delivery of genetic material into a cell. In some embodiments, the vector comprises a first sequence comprising a nucleic acid sequence encoding a self-inactivating transposase and a second sequence comprising a nucleic acid sequence encoding a transposon. In some embodiments, the transposon comprises a gene selected for delivery to a cell. In some embodiments, the gene is flanked by inverted terminal repeats. In some embodiments, the self-inactivating transposase is a Piggyback transposase, a Tn5 transposase, a Sleeping Beauty transposase, a MuA transposase, a Tn552 transposase, a Mariner transposase, or a derivative or analogue thereof. In some embodiments, the first sequence comprises a nucleic acid sequence comprising at least 90%, 91%, 92%, 93%, 94%, 95%, 96%, 96%, 98%, 99%, or 100% sequence identity to SEQ ID NO: 1. In some embodiments, the gene selected for delivery to a cell encodes a fluorescent protein, a chimeric antigen receptor, or a transgene. In some embodiments, the gene selected for delivery to a cell encodes green fluorescent protein (GFP) and comprises a nucleic acid sequence comprising at least 90%, 91%, 92%, 93%, 94%, 95%, 96%, 96%, 98%, 99%, or 100% sequence identity to SEQ ID NO: 8. In some embodiments, the vector is at least 1 kB to 20 kB. In some embodiments, the vector comprises a 5' transposase recognition region and a 3' transposase recognition region. In some embodiments, the second sequence comprises a nucleic acid sequence comprising at least 90%, 91%, 92%, 93%, 94%, 95%, 96%, 96%, 98%, 99%, or 100% sequence identity to SEQ ID NO: 5. In some embodiments, the vector further comprises a sequence encoding a suicide gene. In some embodiments, the suicide gene is thymidine kinase, oxidoreductase, cytosine deaminase, thymidine kinase thymidilate kinase (Tdk::Tmk), or deoxycytidine kinase. In some embodiments, the sequence encoding a suicide gene comprises a nucleic acid sequence comprising at least 90%, 91%, 92%, 93%, 94%, 95%, 96%, 96%, 98%, 99%, or 100% sequence identity to SEQ ID NO: 19. In some embodiments, the vector further comprises a promoter region. In some embodiments, the promoter region is an EF1α promoter comprising a nucleic acid sequence comprising at least 90%, 91%, 92%, 93%, 94%, 95%, 96%, 96%, 98%, 99%, or 100% sequence identity to SEQ ID NO: 7. In some embodiments, the vector further comprises an SV40 poly(A) sequence comprising a nucleic acid sequence comprising at least 90%, 91%, 92%, 93%, 94%, 95%, 96%, 96%, 98%, 99%, or 100% sequence identity to SEQ ID NO: 4. In some embodiments, the vector further comprises an intron. In some embodiments, the intron is positioned within the transposase. In some embodiments, the intron comprises a 5' transposase recognition region. In some embodiments, the intron comprises a nucleic acid sequence comprising at least 90%, 91%, 92%, 93%, 94%, 95%, 96%, 96%, 98%, 99%, or 100% sequence identity to SEQ ID NO: 2. In some embodiments, the vector further comprises one or more of a 5' terminal repeat, a 3' terminal repeat, a core/insulator region, a T2A region, a drug selection gene, a TRPA terminator, an R6K mini origin, an RNA out region, a CMV enhancer region, or a CMV core promoter region. In some embodiments, the drug selection gene encodes dihydrofolate reductase (DHFR), DHFR double mutant (DHFRdm), hygromycin-B phosphotransferase (hph), aminoglycoside phosphotransferase, β-lactamase, chloramphenicol acetyltransferase (CAT), adenosine deaminase (ADA), thymidine kinase (TK), lacz (encoding (β-galactosidase), bleomycin resistance, metallothionein, or xanthine guanine phosphoribosyltransferase (XGPRT). In some embodiments, the drug selection gene comprises a nucleic acid sequence comprising at least 90%, 91%, 92%, 93%, 94%, 95%, 96%, 96%, 98%, 99%, or 100% sequence identity to SEQ ID NO: 10.

Further embodiments described herein relate to a method of expressing a gene of interest in a cell. In some embodiments, the method comprises providing the vector as described herein, introducing the vector into a cell, selecting the cells expressing the gene of interest, and isolating the cells expressing a gene of interest under selective pressure. In some embodiments, the selecting comprises adding a selection reagent, by affinity-based bead selection, or by fluorescence activated cell sorting. In some embodiments, the introducing is performed by electroporation. In some embodiments, the selection reagent comprises an agent for selection. In some embodiments, the agent for selection is methotrexate. In some embodiments, the vector is a vector for delivery of genetic material into a cell. In some embodiments, the vector comprises a first sequence comprising a nucleic acid sequence encoding a self-inactivating transposase and a second sequence comprising a nucleic acid sequence encoding a transposon. In some embodiments, the transposon comprises a gene selected for delivery to a cell. In some embodiments, the gene is flanked by inverted terminal repeats. In some embodiments, the self-inactivating transposase is a PiggyBac transposase, a Tn5 transposase, a Sleeping Beauty transposase, a MuA transposase, a Tn552 transposase, a Mariner transposase, or a derivative or analogue thereof. In some embodiments, the first sequence comprises a nucleic acid sequence comprising at least 90%, 91%, 92%, 93%, 94%, 95%, 96%, 96%, 98%, 99%, or 100% sequence identity to SEQ ID NO: 1. In some embodiments, the gene selected for delivery to a cell encodes a fluorescent protein, a chimeric antigen receptor, or a transgene. In some embodiments, the gene selected for delivery to a cell encodes green fluorescent protein (GFP) and comprises a nucleic acid sequence comprising at least 90%, 91%, 92%, 93%, 94%, 95%, 96%, 96%, 98%, 99%, or 100% sequence identity to SEQ ID NO: 8. In some embodiments, the vector is at least 1 kB to 20 kB. In some embodiments, the vector comprises a 5' transposase recognition region and a 3' transposase recognition region. In some embodiments, the second sequence comprises a nucleic acid sequence comprising at least 90%, 91%, 92%, 93%, 94%, 95%, 96%, 96%, 98%, 99%, or 100% sequence identity to SEQ ID NO: 5. In some embodiments, the vector further comprises a sequence encoding a suicide gene. In some embodiments, the suicide gene is thymidine kinase, oxidoreductase, cytosine deaminase, thymidine kinase thymidilate kinase (Tdk::Tmk), or deoxycytidine kinase. In some embodiments, the sequence encoding a suicide gene comprises a nucleic acid sequence comprising at least 90%, 91%, 92%, 93%, 94%, 95%, 96%, 96%, 98%, 99%, or 100% sequence identity to SEQ ID NO: 19. In some embodiments, the vector further comprises a promoter region. In some embodiments, the promoter region is an EF1α promoter comprising a nucleic acid sequence comprising at least 90%, 91%, 92%, 93%, 94%, 95%, 96%, 96%, 98%, 99%, or 100% sequence identity to SEQ ID NO: 7. In some embodiments, the vector further comprises an SV40 poly(A) sequence comprising a nucleic acid sequence comprising at least 90%, 91%, 92%, 93%, 94%, 95%, 96%, 96%, 98%, 99%, or 100% sequence identity to SEQ ID NO: 4. In some embodiments, the vector further comprises an intron. In some embodiments, the intron is positioned within the transposase. In some embodiments, the intron comprises a 5' transposase recognition region. In some embodiments, the intron comprises a nucleic acid sequence comprising at least 90%, 91%, 92%, 93%, 94%, 95%, 96%, 96%, 98%, 99%, or 100% sequence identity to SEQ ID NO: 2. In some embodiments, the vector further comprises one or more of a 5' terminal repeat, a 3' terminal repeat, a core/insulator region, a T2A region, a drug selection gene, a TRPA terminator, an R6K mini origin, an RNA out region, a CMV enhancer region, or a CMV core promoter region. In some embodiments, the drug selection gene encodes dihydrofolate reductase (DHFR), DHFR double mutant (DHFRdm), hygromycin-B phosphotransferase (hph), aminoglycoside phosphotransferase, (β-lactamase, chloramphenicol acetyltransferase (CAT), adenosine deaminase (ADA), thymidine kinase (TK), lacz (encoding (β-galactosidase), bleomycin resistance, metallothionein, or xanthine guanine phosphoribosyltransferase (XGPRT). In some embodiments, the drug selection gene comprises a nucleic acid sequence comprising at least 90%, 91%, 92%, 93%, 94%, 95%, 96%, 96%, 98%, 99%, or 100% sequence identity to SEQ ID NO: 10.

Some embodiments provided herein relate to a cell comprising the vector as described herein. In some embodiments, the vector is a vector for delivery of genetic material into a cell. In some embodiments, the vector comprises a first sequence comprising a nucleic acid sequence encoding a self-inactivating transposase and a second sequence comprising a nucleic acid sequence encoding a transposon. In some embodiments, the transposon comprises a gene selected for delivery to a cell. In some embodiments, the gene is flanked by inverted terminal repeats. In some embodiments, the self-inactivating transposase is a PiggyBac transposase, a Tn5 transposase, a Sleeping Beauty transposase, a MuA transposase, a Tn552 transposase, a Mariner transposase, or a derivative or analogue thereof. In some embodiments, the first sequence comprises a nucleic acid sequence comprising at least 90%, 91%, 92%, 93%, 94%, 95%, 96%, 96%, 98%, 99%, or 100% sequence identity to SEQ ID NO: 1. In some embodiments, the gene selected for delivery to a cell encodes a fluorescent protein, a chimeric antigen receptor, or a transgene. In some embodiments, the gene selected for delivery to a cell encodes green fluorescent protein (GFP) and comprises a nucleic acid sequence comprising at least 90%, 91%, 92%, 93%, 94%, 95%, 96%, 96%, 98%, 99%, or 100% sequence identity to SEQ ID NO: 8. In some embodiments, the vector is at least 1 kB to 20 kB. In some embodiments, the vector comprises a 5' transposase recognition region and a 3' transposase recognition region. T In some embodiments, the second sequence comprises a nucleic acid sequence comprising at least 90%, 91%, 92%, 93%, 94%, 95%, 96%, 96%, 98%, 99%, or 100% sequence identity to SEQ ID NO: 5. In some embodiments, the vector further comprises a sequence encoding a suicide gene. In some embodiments, the suicide gene is thymidine kinase, oxidoreductase, cytosine deaminase, thymidine kinase thymidilate kinase (Tdk::Tmk), or deoxycytidine kinase. In some embodiments, the sequence encoding a suicide gene comprises a nucleic acid sequence comprising at least 90%, 91%, 92%, 93%, 94%, 95%, 96%, 96%, 98%, 99%, or 100% sequence identity to SEQ ID NO: 19. In some embodiments, the vector further comprises a promoter region. In some embodiments, the promoter region is an EF1α promoter comprising a nucleic acid sequence comprising at least 90%, 91%, 92%, 93%, 94%, 95%, 96%, 96%, 98%, 99%, or 100% sequence identity to SEQ ID NO: 7. In some embodiments, the vector further comprises an SV40 poly(A) sequence comprising a nucleic acid sequence comprising at least 90%, 91%, 92%, 93%, 94%, 95%, 96%, 96%, 98%, 99%, or 100% sequence identity to SEQ ID NO: 4. T In some embodiments, the vector further comprises an intron. In some embodiments, the intron is positioned within the transposase. In some embodiments, the intron comprises a 5' transposase recognition region. In some embodiments, the intron comprises a nucleic acid sequence comprising at least 90%, 91%, 92%, 93%, 94%, 95%, 96%, 96%, 98%, 99%, or 100% sequence identity to SEQ ID NO: 2. In some embodiments, the vector further comprises one or more of a 5' terminal repeat, a 3' terminal repeat, a core/insulator region, a T2A region, a drug selection gene, a TRPA terminator, an R6K mini origin, an RNA out region, a CMV enhancer region, or a CMV core promoter region. In some embodiments, the drug selection gene encodes dihydrofolate reductase (DHFR), DHFR double mutant (DHFRdm), hygromycin-B phosphotransferase (hph), aminoglycoside phosphotransferase, (β-lactamase, chloramphenicol acetyl-transferase (CAT), adenosine deaminase (ADA), thymidine kinase (TK), lacz (encoding (β-galactosidase), bleomycin resistance, metallothionein, or xanthine guanine phosphori-bosyltransferase (XGPRT). In some embodiments, the drug selection gene comprises a nucleic acid sequence compris-ing at least 90%, 91%, 92%, 93%, 94%, 95%, 96%, 96%, 98%, 99%, or 100% sequence identity to SEQ ID NO: 10.

Some embodiments provided herein relate to a method of treating or ameliorating a disease or infection such as a viral disease or a cancer. Exemplary viral diseases that can be treated or ameliorated using the subject methods herein and described in greater detail below include human immuno-deficiency virus (HIV) 1 and 2 infection, Eptein-Barr virus (EBV) infection, or cytomegalo virus (CMV) infection. Exemplary cancers that can be treated or ameliorated using the subject methods herein and described in greater detail below include: Acute Lymphoblastic Leukemia (ALL), Acute Myeloid Leukemia (AML), Adrenocortical Carci-noma, AIDS-Related Cancers, Anal Cancer, Astrocytomas, Brain Cancer, Atypical Teratoid/Rhabdoid Tumors, Central Nervous System cancers, Basal Cell Carcinoma, Bile Duct Cancer, Bladder Cancer, Bone Cancer, Ewing Sarcoma, Osteosarcoma Malignant Fibrous Histiocytoma, Brain Tumors, Breast Cancer, Bronchial Tumors, Burkitt Lym-phoma, Gastrointestinal Carcinoid Tumors, CardiacTumors, Embryonal Tumors, Germ Cell Tumors, Primary CNS Lym-phomas, Cervical Cancers, Cholangiocarcinoma, Chor-doma, Chronic Lymphocytic Leukemia (CLL), Chronic Myelogenous Leukemia (CML), Chronic Myeloprolifera-tive Neoplasms, Colorectal Cancers, Craniopharyngioma, Cutaneous T-Cell Lymphomas, Mycosis Fungoides, Sézary Syndrome, Ductal Carcinomas, Endometrial Cancers, Ependymoma, Esophageal Cancer, Esthesioneuroblastoma, Head and Neck Cancers, Extracranial Germ Cell Tumors, Extragonadal Germ Cell Tumors, Intraocular Melanomas, Retinoblastomas, Fallopian Tube Cancers, Fibrous Histio-cytoma of Bone, Gallbladder Cancers, Gastric Cancers, stomach cancers, Gastrointestinal Carcinoid Tumors, Gas-trointestinal Stromal Tumors (GIST), Germ Cell Tumors, Extragonadal Germ Cell Tumors, Ovarian Germ Cell Tumors, Testicular Cancers, Gestational Trophoblastic Dis-eases, Hairy Cell Leukemia, Hepatocellular Cancers, His-tiocytosis, Langerhans Cell cancers, Hodgkin Lymphomas, Hypopharyngeal Cancers, Intraocular Melanomas, Islet Cell Tumors, Pancreatic Neuroendocrine Tumors, Kaposi Sarco-mas, Kidney (Renal Cell) Cancers, Langerhans Cell Histio-cytosis, Laryngeal Cancers, Leukemia, Lip and Oral Cavity Cancers, Liver Cancer, Lung Cancers (Non-Small Cell and Small Cell), Lymphoma, Male Breast Cancer, Malignant Fibrous Histiocytoma of Bone and Osteosarcoma, Mela-noma, Merkel Cell Carcinoma, Mesothelioma, Metastatic Cancer, Metastatic Squamous Neck Cancer with Occult Primary, Mouth Cancers, Multiple Endocrine Neoplasia Syndromes, Multiple Myeloma/Plasma Cell Neoplasms, Mycosis Fungoides, Myelodysplastic Syndromes, Myelo-dysplastic/Myeloproliferative Neoplasms, Myelogenous Leukemia, Chronic (CML), Myeloid Leukemia, Acute (AML), Myeloproliferative Neoplasms, Chronic Nasal Cav-ity and Paranasal Sinus Cancers, Nasopharyngeal Cancer, Neuroblastoma, Non-Hodgkin Lymphoma, Non-Small Cell Lung Cancers, Oral Cancer, Lip and Oral Cavity Cancer, Oropharyngeal Cancer, Osteosarcoma and Malignant Fibrous Histiocytoma of Bone, Ovarian Cancer, Pancreatic Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasm/Multiple Myeloma, Pleuro-pulmonary Blastomas, Pregnancy Cancer, Primary Central Nervous System (CNS) Lymphomas, Primary Peritoneal Cancer, Prostate Cancer, Rectal Cancer, Recurrent Cancer, Renal Cell Cancer, Retinoblastoma, Rhabdomyosarcoma, Childhood, Salivary Gland Cancers, Sarcomas, Childhood Rhabdomyosarcoma, Childhood Vascular Tumors, Uterine Sarcoma, Sézary Syndrome, Skin Cancer, Small Intestine Cancer, Soft Tissue Sarcoma, Squamous Cell Carcinoma, Squamous Neck Cancer with Occult Primary, Metastatic, T-Cell Lymphoma, Testicular Cancer, Throat Cancer, Naso-pharyngeal Cancer, Oropharyngeal Cancer, Hypopharyngeal Cancer, Thymoma and Thymic Carcinoma, Thyroid Cancer, Transitional Cell Cancer of the Renal Pelvis or Ureter, Urethral Cancer, Uterine Cancer, Uterine Sarcoma, Vaginal Cancer, Vascular Tumors, Vulvar Cancer, or Wilms Tumors.

In some embodiments, the method comprises providing a cell as described herein to a subject. In some embodiments, the cell comprises a vector as described herein. In some embodiments, the subject has a disease or infection. In some embodiments, the vector comprises a gene encoding a chimeric antigen receptor, therapeutic, adaptor, modulator, or other protein intended to modify a disease or infectious state. In some embodiments, the method optionally com-prises measuring or monitoring said subject for an inhibition or amelioration of said disease or infection. In some embodi-ments, the vector is a vector for delivery of genetic material into a cell. In some embodiments, the vector comprises a first sequence comprising a nucleic acid sequence encoding a self-inactivating transposase and a second sequence com-prising a nucleic acid sequence encoding a transposon. In some embodiments, the transposon comprises a gene selected for delivery to a cell. In some embodiments, the gene is flanked by inverted terminal repeats. In some embodiments, the self-inactivating transposase is a Piggy-Bac transposase, a Tn5 transposase, a Sleeping Beauty transposase, a MuA transposase, a Tn552 transposase, a Mariner transposase, or a derivative or analogue thereof. In some embodiments, the first sequence comprises a nucleic acid sequence comprising at least 90%, 91%, 92%, 93%, 94%, 95%, 96%, 96%, 98%, 99%, or 100% sequence identity to SEQ ID NO: 1. In some embodiments, the gene selected for delivery to a cell encodes a fluorescent protein, a chimeric antigen receptor, or a transgene. In some embodi-ments, the gene selected for delivery to a cell encodes green fluorescent protein (GFP) and comprises a nucleic acid sequence comprising at least 90%, 91%, 92%, 93%, 94%, 95%, 96%, 96%, 98%, 99%, or 100% sequence identity to SEQ ID NO: 8. In some embodiments, the vector is at least 1 kB to 20 kB. In some embodiments, the vector comprises a 5' transposase recognition region and a 3' transposase recognition region. T In some embodiments, the second sequence comprises a nucleic acid sequence comprising at least 90%, 91%, 92%, 93%, 94%, 95%, 96%, 96%, 98%, 99%, or 100% sequence identity to SEQ ID NO: 5. In some embodiments, the vector further comprises a sequence encoding a suicide gene. In some embodiments, the suicide gene is thymidine kinase, oxidoreductase, cytosine deami-nase, thymidine kinase thymidilate kinase (Tdk::Tmk), or deoxycytidine kinase. In some embodiments, the sequence encoding a suicide gene comprises a nucleic acid sequence comprising at least 90%, 91%, 92%, 93%, 94%, 95%, 96%, 96%, 98%, 99%, or 100% sequence identity to SEQ ID NO: 19. In some embodiments, the vector further comprises a promoter region. In some embodiments, the promoter region is an EF1α promoter comprising a nucleic acid sequence comprising at least 90%, 91%, 92%, 93%, 94%, 95%, 96%, 96%, 98%, 99%, or 100% sequence identity to SEQ ID NO: 7. In some embodiments, the vector further comprises an SV40 poly(A) sequence comprising a nucleic acid sequence comprising at least 90%, 91%, 92%, 93%, 94%, 95%, 96%, 96%, 98%, 99%, or 100% sequence identity to SEQ ID NO: 4. T In some embodiments, the vector further comprises an intron. In some embodiments, the intron is positioned within the transposase. In some embodiments, the intron comprises a 5' transposase recognition region. In some embodiments, the intron comprises a nucleic acid sequence comprising at least 90%, 91%, 92%, 93%, 94%, 95%, 96%, 96%, 98%, 99%, or 100% sequence identity to SEQ ID NO: 2. In some embodiments, the vector further comprises one or more of a 5' terminal repeat, a 3' terminal repeat, a core/insulator region, a T2A region, a drug selection gene, a TRPA terminator, an R6K mini origin, an RNA out region, a CMV enhancer region, or a CMV core promoter region. In some embodiments, the drug selection gene encodes dihydrofolate reductase (DHFR), DHFR double mutant (DHFRdm), hygromycin-B phosphotransferase (hph), aminoglycoside phosphotransferase, β-lactamase, chloramphenicol acetyltransferase (CAT), adenosine deaminase (ADA), thymidine kinase (TK), lacz (encoding (β-galactosidase), bleomycin resistance, metallothionein, or xanthine guanine phosphoribosyltransferase (XGPRT). In some embodiments, the drug selection gene comprises a nucleic acid sequence comprising at least 90%, 91%, 92%, 93%, 94%, 95%, 96%, 96%, 98%, 99%, or 100% sequence identity to SEQ ID NO: 10.

Accordingly, some aspects described herein relate to the following numbered alternatives:

1. A vector for delivery of genetic material into a cell, the vector comprising: a first sequence comprising a nucleic acid sequence encoding a self-inactivating transposase; and a second sequence comprising a nucleic acid sequence encoding a transposon, wherein the transposon comprises a gene selected for delivery to a cell, wherein the gene is flanked by inverted terminal repeats.

2. The vector of alternative 1, wherein the self-inactivating transposase is a PiggyBac transposase, a Tn5 transposase, a Sleeping Beauty transposase, a MuA transposase, a Tn552 transposase, a Mariner transposase, or a derivative or analogue thereof.

3. The vector of alternative 1 or 2, wherein the first sequence comprises a nucleic acid sequence comprising at least 90%, 91%, 92%, 93%, 94%, 95%, 96%, 96%, 98%, 99%, or 100% sequence identity to SEQ ID NO: 1.

4. The vector of any one of alternatives 1-3, wherein the gene selected for delivery to a cell encodes a fluorescent protein, a chimeric antigen receptor, or a transgene.

5. The vector of any one of alternatives 1-3, wherein the gene selected for delivery to a cell encodes green fluorescent protein (GFP) and comprises a nucleic acid sequence comprising at least 90%, 91%, 92%, 93%, 94%, 95%, 96%, 96%, 98%, 99%, or 100% sequence identity to SEQ ID NO: 8.

6. The vector of any one of alternatives 1-5, wherein the vector is at least 1 kB to 20 kB.

7. The vector of any one of alternatives 1-6, wherein the vector comprises a 5' transposase recognition region and a 3' transposase recognition region.

8. The vector of any one of alternatives 1-7, wherein the second sequence comprises a nucleic acid sequence comprising at least 90%, 91%, 92%, 93%, 94%, 95%, 96%, 96%, 98%, 99%, or 100% sequence identity to SEQ ID NO: 5.

9. The vector of any one of alternatives 1-8, wherein the vector further comprises a sequence encoding a suicide gene.

10. The vector of alternative 9, wherein the suicide gene is thymidine kinase, oxidoreductase, cytosine deaminase, thymidine kinase thymidilate kinase (Tdk::Tmk), or deoxycytidine kinase.

11. The vector of alternative 9, wherein the sequence encoding a suicide gene comprises a nucleic acid sequence comprising at least 90%, 91%, 92%, 93%, 94%, 95%, 96%, 96%, 98%, 99%, or 100% sequence identity to SEQ ID NO: 19.

12. The vector of any one of alternatives 1-11, wherein the vector further comprises a promoter region.

13. The vector of alternative 12, wherein the promoter region is an EF1α promoter comprising a nucleic acid sequence comprising at least 90%, 91%, 92%, 93%, 94%, 95%, 96%, 96%, 98%, 99%, or 100% sequence identity to SEQ ID NO: 7.

14. The vector of any one of alternatives 1-13, wherein the vector further comprises an SV40 poly(A) sequence comprising a nucleic acid sequence comprising at least 90%, 91%, 92%, 93%, 94%, 95%, 96%, 96%, 98%, 99%, or 100% sequence identity to SEQ ID NO: 4.

15. The vector of any one of alternatives 1-14, wherein the vector further comprises an intron, wherein the intron is positioned within the transposase, and wherein the intron comprises a 5' transposase recognition region.

16. The vector of alternative 15, wherein the intron comprises a nucleic acid sequence comprising at least 90%, 91%, 92%, 93%, 94%, 95%, 96%, 96%, 98%, 99%, or 100% sequence identity to SEQ ID NO: 2.

17. The vector of any one of alternatives 1-16, wherein the vector further comprises one or more of a 5' terminal repeat, a 3' terminal repeat, a core/insulator region, a T2A region, a drug selection gene, a TRPA terminator, an R6K mini origin, an RNA out region, a CMV enhancer region, or a CMV core promoter region.

18. The vector of alternative 17, wherein the drug selection gene encodes dihydrofolate reductase (DHFR), DHFR double mutant (DHFRdm), hygromycin-B phosphotransferase (hph), aminoglycoside phosphotransferase, β-lactamase, chloramphenicol acetyltransferase (CAT), adenosine deaminase (ADA), thymidine kinase (TK), lacz (encoding (β-galactosidase), bleomycin resistance, metallothionein, or xanthine guanine phosphoribosyltransferase (XGPRT).

19. The vector of alternative 17, wherein the drug selection gene comprises a nucleic acid sequence comprising at least 90%, 91%, 92%, 93%, 94%, 95%, 96%, 96%, 98%, 99%, or 100% sequence identity to SEQ ID NO: 10.

20. A method of expressing a gene of interest in a cell, comprising, providing the vector of any one of alternatives 1-19; introducing the vector into a cell; selecting the cells expressing the gene of interest; and isolating the cells expressing a gene of interest under selective pressure.

21. The method of alternative 20, wherein the selecting comprises adding a selection reagent, by affinity-based bead selection, or by fluorescence activated cell sorting 22. The method of any one of alternatives 20-21, wherein the introducing is performed by electroporation.

23. The method of alternative 21, wherein the selection reagent comprises an agent for selection.

24. The method of alternative 23, wherein the agent for selection is methotrexate.

25. A cell comprising the vector of any one of alternatives 1-19.

26. The cell of alternative 25, wherein said cell is a primary cell, such as a T-cell, preferably a human T-cell, or a stem cell, preferably a human stem cell, for example a CD34+ human stem cell.

27. A method of treating or ameliorating a disease or infection comprising: providing the cell of alternative 25 or 26 to a subject, which has a disease or infection, wherein the vector comprises a gene encoding a chimeric antigen receptor, therapeutic, adaptor, modulator, or other protein intended to modify a disease or infectious state; and optionally, measuring or monitoring said subject for an inhibition or amelioration of said disease or infection.

28. The method of alternative 27, wherein said disease is a viral disease such as HIV 1 or 2, EBV, or CMV or a cancer such as Acute Lymphoblastic Leukemia (ALL), Acute Myeloid Leukemia (AML), Adrenocortical Carcinoma, AIDS-Related Cancers, Anal Cancer, Astrocytomas, Brain Cancer, Atypical Teratoid/Rhabdoid Tumors, Central Nervous System cancers, Basal Cell Carcinoma, Bile Duct Cancer, Bladder Cancer, Bone Cancer, Ewing Sarcoma, Osteosarcoma Malignant Fibrous Histiocytoma, Brain Tumors, Breast Cancer, Bronchial Tumors, Burkitt Lymphoma, Gastrointestinal Carcinoid Tumors, CardiacTumors, Embryonal Tumors, Germ Cell Tumors, Primary CNS Lymphomas, Cervical Cancers, Cholangiocarcinoma, Chordoma, Chronic Lymphocytic Leukemia (CLL), Chronic Myelogenous Leukemia (CIVIL), Chronic Myeloproliferative Neoplasms, Colorectal Cancers, Craniopharyngioma, Cutaneous T-Cell Lymphomas, Mycosis Fungoides, Sézary Syndrome, Ductal Carcinomas, Endometrial Cancers, Ependymoma, Esophageal Cancer, Esthesioneuroblastoma, Head and Neck Cancers, Extracranial Germ Cell Tumors, Extragonadal Germ Cell Tumors, Intraocular Melanomas, Retinoblastomas, Fallopian Tube Cancers, Fibrous Histiocytoma of Bone, Gallbladder Cancers, Gastric Cancers, stomach cancers, Gastrointestinal Carcinoid Tumors, Gastrointestinal Stromal Tumors (GIST), Germ Cell Tumors, Extragonadal Germ Cell Tumors, Ovarian Germ Cell Tumors, Testicular Cancers, Gestational Trophoblastic Diseases, Hairy Cell Leukemia, Hepatocellular Cancers, Histiocytosis, Langerhans Cell cancers, Hodgkin Lymphomas, Hypopharyngeal Cancers, Intraocular Melanomas, Islet Cell Tumors, Pancreatic Neuroendocrine Tumors, Kaposi Sarcomas, Kidney (Renal Cell) Cancers, Langerhans Cell Histiocytosis, Laryngeal Cancers, Leukemia, Lip and Oral Cavity Cancers, Liver Cancer, Lung Cancers (Non-Small Cell and Small Cell), Lymphoma, Male Breast Cancer, Malignant Fibrous Histiocytoma of Bone and Osteosarcoma, Melanoma, Merkel Cell Carcinoma, Mesothelioma, Metastatic Cancer, Metastatic Squamous Neck Cancer with Occult Primary, Mouth Cancers, Multiple Endocrine Neoplasia Syndromes, Multiple Myeloma/Plasma Cell Neoplasms, Mycosis Fungoides, Myelodysplastic Syndromes, Myelodysplastic/Myeloproliferative Neoplasms, Myelogenous Leukemia, Chronic (CIVIL), Myeloid Leukemia, Acute (AML), Myeloproliferative Neoplasms, Chronic Nasal Cavity and Paranasal Sinus Cancers, Nasopharyngeal Cancer, Neuroblastoma, Non-Hodgkin Lymphoma, Non-Small Cell Lung Cancers, Oral Cancer, Lip and Oral Cavity Cancer, Oropharyngeal Cancer, Osteosarcoma and Malignant Fibrous Histiocytoma of Bone, Ovarian Cancer, Pancreatic Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasm/ Multiple Myeloma, Pleuropulmonary Blastomas, Pregnancy Cancer, Primary Central Nervous System (CNS) Lymphomas, Primary Peritoneal Cancer, Prostate Cancer, Rectal Cancer, Recurrent Cancer, Renal Cell Cancer, Retinoblastoma, Rhabdomyosarcoma, Childhood, Salivary Gland Cancers, Sarcomas, Childhood Rhabdomyosarcoma, Childhood Vascular Tumors, Uterine Sarcoma, Sézary Syndrome, Skin Cancer, Small Intestine Cancer, Soft Tissue Sarcoma, Squamous Cell Carcinoma, Squamous Neck Cancer with Occult Primary, Metastatic, T-Cell Lymphoma, Testicular Cancer, Throat Cancer, Nasopharyngeal Cancer, Oropharyngeal Cancer, Hypopharyngeal Cancer, Thymoma and Thymic Carcinoma, Thyroid Cancer, Transitional Cell Cancer of the Renal Pelvis or Ureter, Urethral Cancer, Uterine Cancer, Uterine Sarcoma, Vaginal Cancer, Vascular Tumors, Vulvar Cancer, or Wilms Tumors.

29. Use of the vector of any one of alternatives 1-19 or the cell of alternatives 25 or 26 as a medicament.

30. The vector of any one of alternatives 1-19 or the cell of alternatives 25 or 26 for use as a medicament for treating or ameliorating a viral disease such as HIV 1 or 2, EBV, or CMV or a cancer such as Acute Lymphoblastic Leukemia (ALL), Acute Myeloid Leukemia (AML), Adrenocortical Carcinoma, AIDS-Related Cancers, Anal Cancer, Astrocytomas, Brain Cancer, Atypical Teratoid/Rhabdoid Tumors, Central Nervous System cancers, Basal Cell Carcinoma, Bile Duct Cancer, Bladder Cancer, Bone Cancer, Ewing Sarcoma, Osteosarcoma Malignant Fibrous Histiocytoma, Brain Tumors, Breast Cancer, Bronchial Tumors, Burkitt Lymphoma, Gastrointestinal Carcinoid Tumors, CardiacTumors, Embryonal Tumors, Germ Cell Tumors, Primary CNS Lymphomas, Cervical Cancers, Cholangiocarcinoma, Chordoma, Chronic Lymphocytic Leukemia (CLL), Chronic Myelogenous Leukemia (CIVIL), Chronic Myeloproliferative Neoplasms, Colorectal Cancers, Craniopharyngioma, Cutaneous T-Cell Lymphomas, Mycosis Fungoides, Sézary Syndrome, Ductal Carcinomas, Endometrial Cancers, Ependymoma, Esophageal Cancer, Esthesioneuroblastoma, Head and Neck Cancers, Extracranial Germ Cell Tumors, Extragonadal Germ Cell Tumors, Intraocular Melanomas, Retinoblastomas, Fallopian Tube Cancers, Fibrous Histiocytoma of Bone, Gallbladder Cancers, Gastric Cancers, stomach cancers, Gastrointestinal Carcinoid Tumors, Gastrointestinal Stromal Tumors (GIST), Germ Cell Tumors, Extragonadal Germ Cell Tumors, Ovarian Germ Cell Tumors, Testicular Cancers, Gestational Trophoblastic Diseases, Hairy Cell Leukemia, Hepatocellular Cancers, Histiocytosis, Langerhans Cell cancers, Hodgkin Lymphomas, Hypopharyngeal Cancers, Intraocular Melanomas, Islet Cell Tumors, Pancreatic Neuroendocrine Tumors, Kaposi Sarcomas, Kidney (Renal Cell) Cancers, Langerhans Cell Histiocytosis, Laryngeal Cancers, Leukemia, Lip and Oral Cavity Cancers, Liver Cancer, Lung Cancers (Non-Small Cell and Small Cell), Lymphoma, Male Breast Cancer, Malignant Fibrous Histiocytoma of Bone and Osteosarcoma, Melanoma, Merkel Cell Carcinoma, Mesothelioma, Metastatic Cancer, Metastatic Squamous Neck Cancer with Occult Primary, Mouth Cancers, Multiple Endocrine Neoplasia Syndromes, Multiple Myeloma/Plasma Cell Neoplasms, Mycosis Fungoides, Myelodysplastic Syndromes, Myelodysplastic/Myeloproliferative Neoplasms, Myelogenous Leukemia, Chronic (CIVIL), Myeloid Leukemia, Acute (AML), Myeloproliferative Neoplasms, Chronic Nasal Cavity and Paranasal Sinus Cancers, Nasopharyngeal Cancer, Neuroblastoma, Non-Hodgkin Lymphoma, Non-Small Cell Lung Cancers, Oral Cancer, Lip and Oral Cavity Cancer, Oropharyngeal Cancer, Osteosarcoma and Malignant Fibrous Histiocytoma of Bone, Ovarian Cancer, Pancreatic Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasm/Multiple Myeloma, Pleuropulmonary Blastomas, Pregnancy Cancer, Primary Central Nervous System (CNS) Lymphomas, Primary Peritoneal Cancer, Prostate Cancer, Rectal Cancer, Recurrent Cancer, Renal Cell Cancer, Retinoblastoma, Rhabdomyosarcoma, Childhood, Salivary Gland Cancers, Sarcomas, Childhood Rhabdomyosarcoma, Childhood Vascular Tumors, Uterine Sarcoma, Sezary Syndrome, Skin Cancer, Small Intestine Cancer, Soft Tissue Sarcoma, Squamous Cell Carcinoma, Squamous Neck Cancer with Occult Primary, Metastatic, T-Cell Lymphoma, Testicular Cancer, Throat Cancer, Nasopharyngeal Cancer, Oropharyngeal Cancer, Hypopharyngeal Cancer, Thymoma and Thymic Carcinoma, Thyroid Cancer, Transitional Cell Cancer of the Renal Pelvis or Ureter, Urethral Cancer, Uterine Cancer, Uterine Sarcoma, Vaginal Cancer, Vascular Tumors, Vulvar Cancer, or Wilms Tumors.

DETAILED DESCRIPTION

Figure 1:
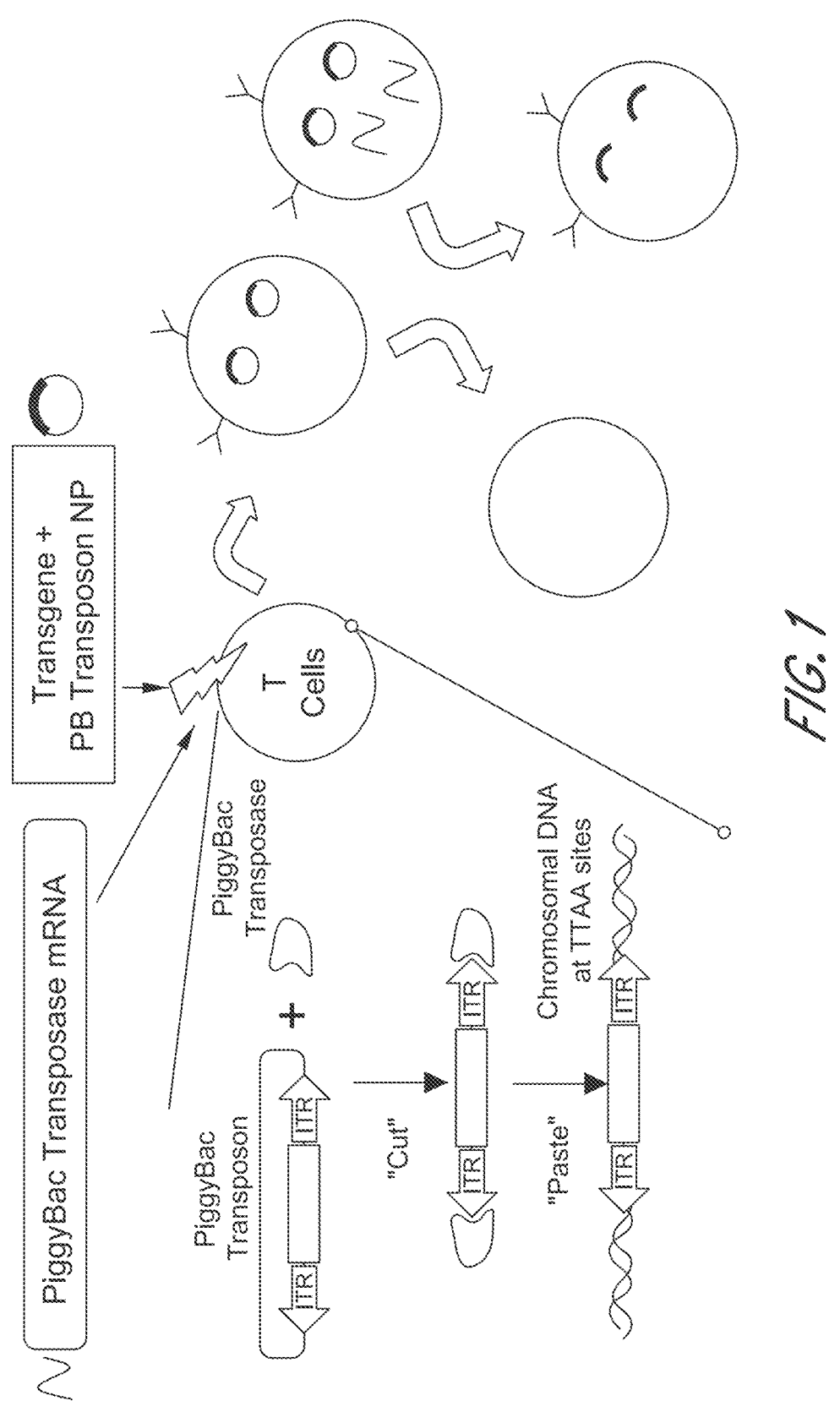
FIG. 1 shows a schematic of a traditional PiggyBac transposase system including electroporation of PiggyBac transposase mRNA and electroporation of a DNA transgene+PiggyBac transposon.

Some embodiments provided herein relate to gene delivery systems and methods using a single plasmid that carries a self-inactivating transposase gene and a corresponding transposon. Some embodiments include nucleic acids having certain sequences, vector including such nucleic acids, and compositions including the vectors.

Some embodiments provided herein relate to a circular vector, such as a plasmid or minicircle, comprising a self-inactivating transposase gene and a transposon. In some embodiments, the circular vector comprises a nucleic acid encoding a transposase gene, and a first and a second transposase recognition site. In some embodiments, the first transposase recognition site located within the transposase gene. In some embodiments, the first transposase recognition is located within an intron in the transposase gene.

In some embodiments, the circular vector is introduced into a cell. In some embodiments, transposase gene is transcribed and translated in a cell. In some such embodiments, the vector in the cell can also be a substrate for the transposase protein. For example, the transposase recognition sites of the vector can be substrates for the transposase to transpose nucleic acid sequences of the vector into host nucleic acids, such as a host genome. In some such embodiments, transposition of vector sequences into host nucleic acids results in an interrupted and inactivated copy of the transposase gene or portion thereof in the host nucleic acids. In some embodiments, the vector can include a gene of interest, such as a promoter and a polynucleotide encoding a polypeptide. In some such embodiments, transposition of vector sequences into host nucleic acids can result in integration of a functional copy of the gene of interest into the host nucleic acids.

In the detailed description herein, reference is made to the accompanying drawings, which form a part hereof. In the drawings, similar symbols typically identify similar components, unless context dictates otherwise. The illustrative alternatives described in the detailed description, drawings, and claims are not meant to be limiting. Other alternatives may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Definitions

In the description that follows, several terms are used extensively. The following definitions are provided to facilitate understanding of the present alternatives. Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, NY 1994); Sambrook et al., Molecular Cloning, A Laboratory Manual, Cold Springs Harbor Press (Cold Springs Harbor, N Y 1989). For purposes of the present disclosure, the following terms are defined below.

The articles "a" and "an" are used herein to refer to one or to more than one (for example, to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight, or length.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process comprises at least the recited steps, but may include additional steps. When used in the context of a compound, composition or device, the term "comprising" means that the compound, composition or device comprises at least the recited features or components but may also include additional features or components.

Some alternatives disclosed herein relate to a genetic engineering system carried in a single vector. In some embodiments, the vector comprises a self-inactivating transposase gene and a corresponding transposon, thereby providing a genetic engineering system incorporated into a single vector system. Some embodiments provided herein relate to methods of making and using the self-inactivating transposase/transposon system and using this system in a cell, such as a primary cell, preferably a human primary cell, e.g., a T-cell, stem cell or CD34⁺ stem cell.

As used herein, the term "self-inactivating" refers to a system, such as a vector system that contains a non-functional or modified 3' terminal repeat sequence, which is copied to the 5' end of the vector genome during integration, resulting in inactivation of promoter activity.

14

Figure 2:
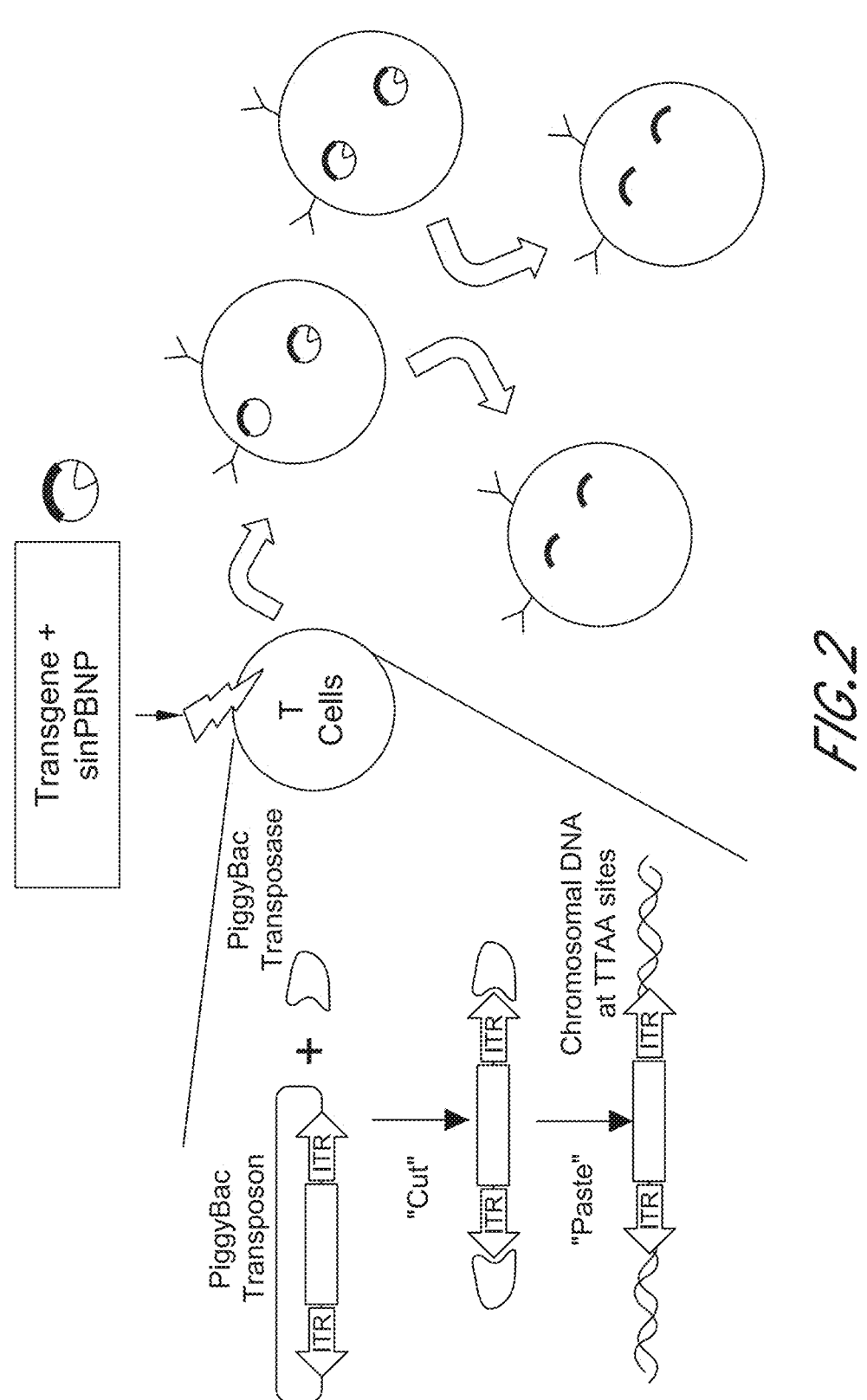
FIG. 2 shows a schematic of electroporation using a single plasmid system as set forth in some embodiments described herein, wherein a self-inactivating PiggyBac (sinPB) is electroporated together with a transgene in a single plasmid containing a PiggyBac transposon.

Transposon-transposase systems insert foreign genetic material into a cell of interest. Typically, this is done by delivering the transposon and transposase separately, due to safety reasons involving potential integrations of transposase genes into a host cell, as shown in FIG. 1. Thus, gene delivery using a transposon/transposase system requires a two-components, which increases cost and complexity while decreasing efficiency. However, described herein are single-component self inactivating transpoase-transposon systems for genetic engineering, as schematically depicted in FIG. 2.

As used herein, the term "vector" has its plain and ordinary meaning when read in light of the specification, and may include but is not limited to, for example, a polynucleotide construct, typically a plasmid or a virus, used to transmit genetic material to a host cell. Vectors can be, for example, viruses, plasmids, cosmids, or phage. A vector as used herein can be composed of either DNA or RNA. In some alternatives, a vector is composed of DNA. An "expression vector" is a vector that is capable of directing the expression of a protein encoded by one or more genes carried by the vector when it is present in the appropriate environment. Vectors are preferably capable of autonomous replication. Typically, an expression vector comprises various components for efficient gene expression, and may include, for example, a transcription promoter, a gene of interest (GOI), and a transcription terminator. Gene expression is usually placed under the control of a promoter, and a gene is said to be "operably linked to" the promoter.

As used herein, "transposon" or "transposable element (TE)" refers to a DNA sequence that is capable of transposition within a gene. In some embodiments, the transposon is a PiggyBac (PB) transposon, which is a DNA derived from a moth called Trichopulsia ni in Lepidopteran and excised from the genomic DNA by a PB transposase. To be more specific, the PB transposon refers to a DNA, at both ends of which PB inverted-repeat transposable elements (ITRs) recognized specifically by the transposase are disposed. In some embodiments, inverted terminal repeats flank the gene of interest, and all three pieces (the gene of interest, with an inverted terminal repeat on either end) make up a transposon region.

As used herein, "transposase" refers to an enzyme that binds to the end of a transposon and catalyzes the movement of the transposon to another part of the genome by a cut-and-paste mechanism or a replicative-transposition mechanism. Exemplary transposases that can be used with certain embodiments provided herein include (or are encoded by): PiggyBac transposase, Tn5 transposase (see Reznikoff et al., Biochem. Biophys. Res. Commun. 1999, 266, 729-734), Sleeping Beauty (SB) transposase, Vibrio harveyi (transposase characterized by Agilent and used in SureSelect QXT product), MuA transposase and a Mu transposase recognition site comprising R1 and R2 end sequences (Mizuuchi, K., Cell, 35: 785, 1983; Savilahti, H, et al., EMBO J., 14:4893, 1995), Staphylococcus aureus Tn552 (Colegio, O. et al., J. Bacteriol., 183:2384-8, 2001; Kirby, C. et al., Mol. Microbiol., 43:173-86, 2002), Ty1 (Devine & Boeke, Nucleic Acids Res., 22:3765-72, 1994 and PCT Publ. No. WO95/23875), Transposon Tn7 (Craig, N. L., Science, 271:1512, 1996; Craig, N. L., Curr. Top. Microbiol. Immunol., 204:27-48, 1996), Tn/O and IS10 (Kleckner N. et al., Curr. Top. Microbiol. Immunol., 204: 49-82, 1996), Mariner transposase (Lampe, D. J. et al., EMBO J., 15:5470-9, 1996), Tc1 (Plasterk, R. H., Curr. Top. Microbiol. Immunol., 204:125-43, 1996), P Element (Gloor, G. B., Methods Mol. Biol., 260:97-114, 2004), Tn3 (Ichikawa & Ohtsubo, J. Biol. Chem., 265:18829-32, 1990), bacterial insertion sequences (Ohtsubo & Sekine, Curr. Top. Microbiol. Immunol. 204:1-26, 1996), retroviruses (Brown et al., Proc. Natl. Acad. Sci. USA, 86:2525-9, 1989), and retrotransposon of yeast (Boeke & Corces, Ann. Rev. Microbiol. 43:403-34, 1989). More examples include IS5, Tn10, Tn903, IS911, and engineered versions of transposase family enzymes (Zhang et al., (2009) PLoS Genet. 5:e1000689. Epub October 16; Wilson C. et al. (2007) J. Microbiol. Methods 71:332-5), each of the references cited herein with respect to the transposase is expressly incorporated herein by reference in its entirety. The systems and methods described herein may also include combinations of transposases, and not just a single transposase. Further, more active versions of transposases may be used. In some embodiments, the transposase is a PiggyBac transposase, or an active mutant thereof.

Vectors

In some embodiments, the compositions, systems, and methods described herein concern or utilize a vector for delivery of genetic material into a cell comprising a nucleic acid sequence encoding a transposase and a corresponding transposon. In some embodiments, the vector comprises a first sequence comprising a nucleic acid sequence encoding a self-inactivating transposase and a second sequence comprising a nucleic acid sequence encoding a transposon. In some embodiments, the vector further comprises a nucleic acid sequence encoding a gene of interest for delivery into a cell.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded. In some alternatives described herein, a gene delivery vector having a self-inactivating transposase system is provided. "Oligonucleotide" can be used interchangeable with nucleic acid and can refer to DNA or RNA, either double stranded or a single stranded portion of DNA or RNA. Nucleic acid sequences may be described herein with a SEQ ID NO, and are described throughout the application and included in Appendix I. In some alternatives, a nucleotide sequence described herein is 85%, 86%, 87%, 88%, 89%, 90%, 91%, 92%, 93%, 94%, 95%, 96%, 97%, 98%, 99% or 100% identical, or is within a range defined by any two of the aforementioned percentages, to a sequence of any one of SEQ ID NOs: 1-20.

A "gene" is the molecular unit of heredity of a living organism, describing some stretches of deoxyribonucleic acids (DNA) and ribonucleic acids (RNA) that code for a polypeptide or for an RNA chain that has a function in the organism, and can be a locatable region in the genome of an organism. In some embodiments, the vector includes a nucleic acid sequence encoding a gene of interest, which is a gene for delivery to a cell. In some embodiments, the gene of interest may be any gene for expression in a cell, such as in a mammalian cell. For example, the gene of interest may be any gene encoding a product of interest that upon expression, imparts a desirable characteristic. For example, a gene of interest may be a marker, such as a fluorescent protein, such as a green fluorescent protein (GFP), a therapeutic gene, such as a chimeric antigen receptor, or other transgene of interest.

Figure 3:
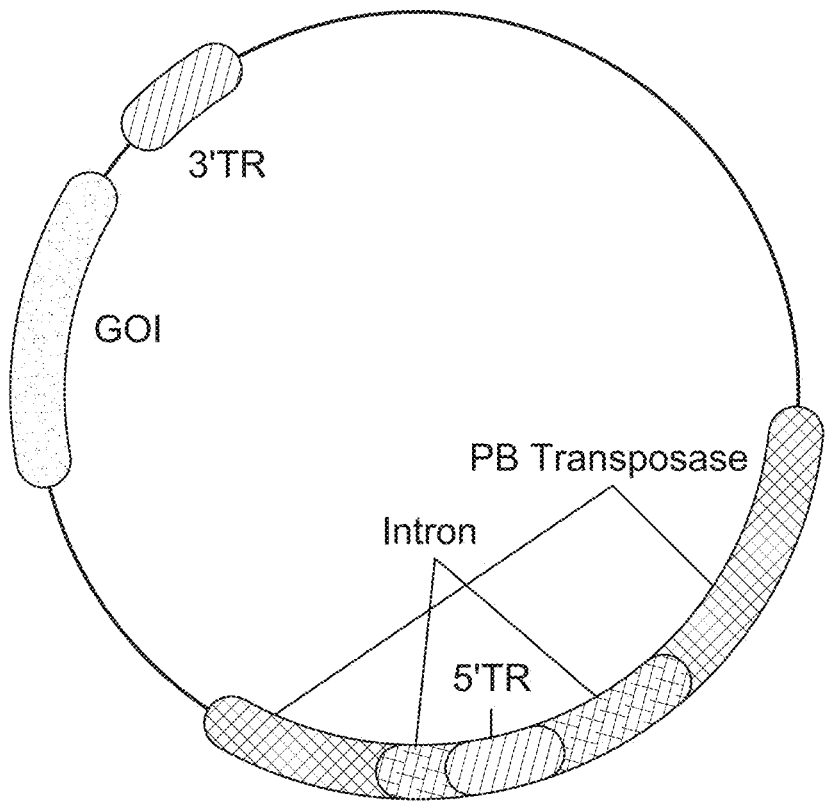
FIG. 3 shows a schematic representation of a self-inactivating PiggyBac transposase construct.
Figure 4:
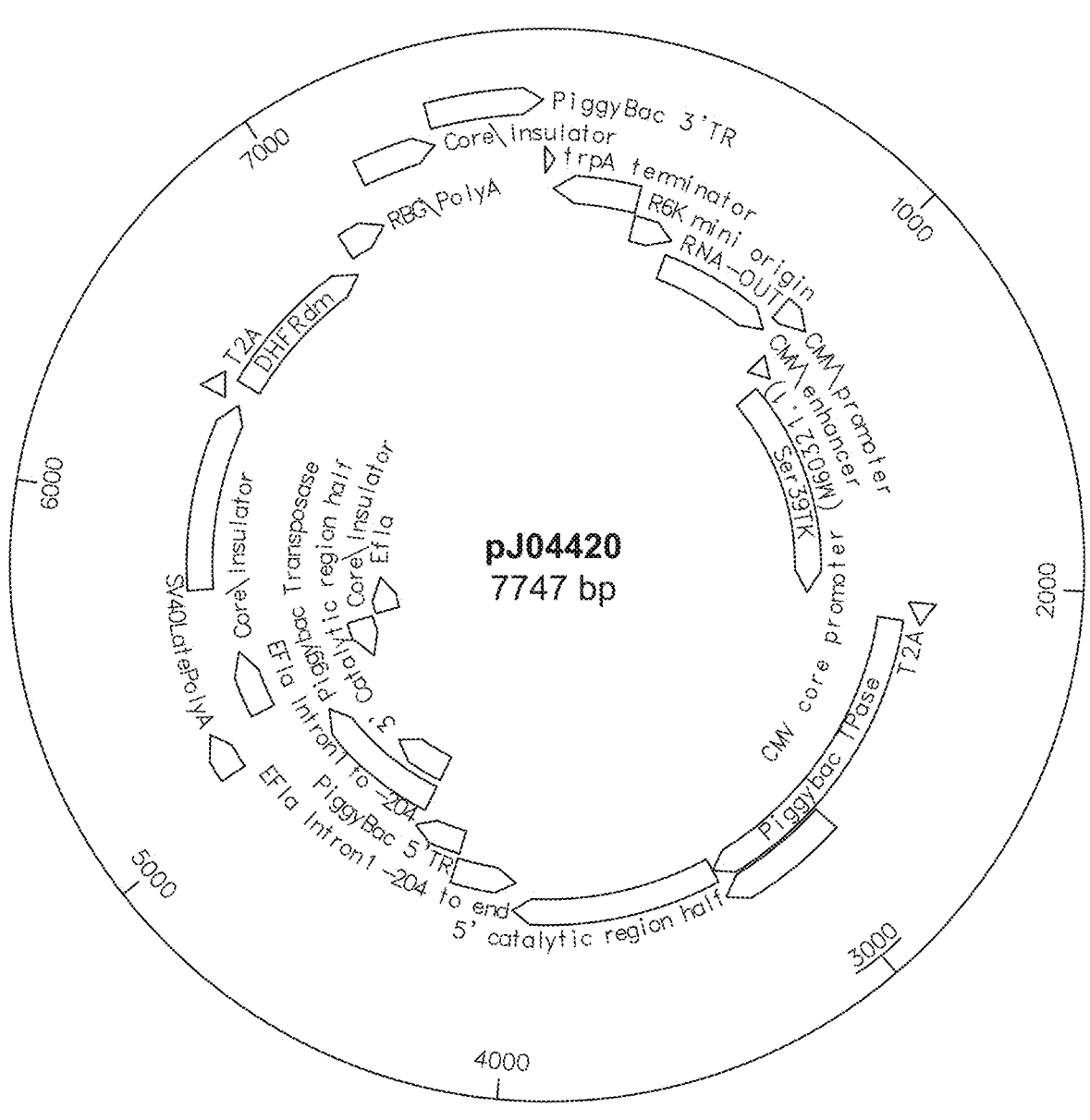
FIG. 4 shows a detailed schematic representation of an embodiment of a sinPB construct, showing various components of the construct. The backbone contains Ser39TK suicide switch and R6K region, useful for backbone detection.

In some embodiments, the vector comprises a nucleic acid sequence that encodes various additional components for delivery of the gene of interest. With reference to FIG. 3, a vector of some of the embodiments described herein may include a backbone, a gene of interest (GOI) flanked by a 3' terminal repeat (3'TR) and a 5'TR. The vector of FIG. 3 also includes a PB transposase having an intron inserted therein. In some embodiments, the 5'TR is inserted within the intron making the transposase self-inactivating. FIG. 4 provides additional details of an exemplary self-inactivating transposase vector. As shown in FIG. 4, the vector includes a PB transposase with an intron (EF1α) inserted therein, and a transposon having a gene of interest (in this example, eGFP). The vector shown in this example comprises additional components, e.g., promoter regions, a suicide gene, a T2A region, and others, as are described herein in greater detail.

In some embodiments, the vector may comprise a transposase region and a transposon region. In some embodiments, a transposase region includes a transposase, an intron, and a promoter. In some embodiments, a transposon region comprises a gene of interest, a promoter, a drug selection gene, or other components.

More specifically, in some embodiments, a vector may comprise a transposase region having a PiggyBac transposase 5' catalytic region comprising a nucleic acid sequence of SEQ ID NO: 1: (ATGGGCAGCAGCCTGGACGACGAGCACATCCTGTCTGCCCTGCTGCAATCCGACGATGAGCTCGTGGGCGAGGACAGCGACAGCGAGATCAGCGATCACGTGTCCGAG GACGACGTGCAGTCCGACACCGAGGAAGCCTTCATCGACGAGGTGCACGAAGTG CAGCCTACCAGCAGCGGCTCCGAGATCCTGGACGAGCAGAACGTGATCGAGCAGCCCGGAAGCTCCCTGGCCAGCAACAGAATCCTGACCCTGCCCCAGCGGACCATC CGGGGCAAGAACAAGCACTGCTGGTCCACCAGCAAGAGCACCCGGCGGTCCAGA GTGTCCGCCCTGAATATCGTGCGGAGCCAGAGGGGGCCCCACCCGGATGTGCAGA AACATCTACGACCCCCTGCTGTGCTTCAAGCTGTTCTTCACCGACGAGATCATCT CTGAGATCGTGAAGTGGACCAACGCCGAGATCTCCCTGAAGCGGCGCGAGTCTA TGACCGGCGCCACCTTCAGAGACACCAACGAGGACGAGATCTACGCCTTCTTCG GCATCCTCGTGATGACCGCCGTGCGGAAGGACA-ACCACATGAGCACCGACGACC TGTTCGACCGGT-CCCTGAGCATGGTGTACGTGTCCGTGATGAGCC-GGGACAGATT CGACTTCCTGATCCGGTGCCTGCG-GATGGACGACAAGAGCATCAGACCCACCCT GCGCGAGAACGACGTGTTCACCCCTGTGCGGAA-GATCTGGGACCTGTTCATCCAC CAGTGCATCCA-GAACTACACCCCTGGCGCCCACCTGACCATCGA-CGAACAGCTG CTGGGCTTCAGAGGCCGGTGCCCC-TTCAGAATGTACATCCCCAACAAGCCCTCTA-AGTACGGCATCAAGATCCTGATGATGTGCGA-CAGCGGCACCAAGTACATGATCA ACGGCATGCCC-TACCTGGGCAGAGGCACCCAGACAAATGGCGTGC-CACTGGGCG AGTACTACGTGAAAGAACT-GAGCAAGCCTGTGCACGGCTCCTGCCGGAACATCA CCTGTGACAACTGGTTCACCTCCATCCCCCTGGC-CAAGAATCTGCTGCAGGAACC CTACAAGCTGAC-AATCGTGGGCACCGTGCGGTCCAACAAGCGCGA-GATTCCCGA G). In some embodiments, the transposase catalytic region is 85%, 86%, 87%, 88%, 89%, 90%, 91%, 92%, 93%, 94%, 95%, 96%, 97%, 98%, 99% or 100% identical, or is within a range defined by any two of the aforementioned percentages, to a sequence of SEQ ID NO: 1.

In some embodiments, the transposase region further comprises an intron, such as an EF1α intron comprising a nucleic acid sequence of SEQ ID NO: 2: (GTAAGTGCCGTGTGTGGTTCCCGCGGGCCTGGCC-TCTTTACGGGTTATGGCCCTT GCGTGCCTTGAAT-TACTTCCACGCCCCTGGCTGCAGTACGTGATTCTT-GATCCCG AGCTTCGGGTTGGAAGTGGGTGG-GAGAGTTCGAGGCCTTGCGCTTAAGGAGCCC CTTCGCCTCGTGCTTGAGTTGAGGCCTGGCTT-GGGCGCTGGGGCCGCCGCGTGCG AATCTGGTGG-CACCTTCGCGCCTGTCTCGCTGCTTTCGATAAGTC-TCTAGCCATTT AAAATTTTTGATGACC- TGCTGCGA-CGCTTTTTTTCTGGCAAGATAGTCTTGTAAAT GCGGGCCAAGATCTGCACACTGGTATTTCGGT-TTTTGGGGCCGCGGGCGGCGAC GGGGCCC-GTGCGTCCCAGCGCACATGTTCGGCGAGGCGGG-GCCTGCGAGCGCGG CCACCGAGAATCGGACG-GGGGTAGTCTCAAGCTGGCCGGCCTGCTCTGG-TGCCT GGCCTCGCGCCGCCGTGTATCGCCCCGCC-CTGGGCGGCAAGGCTGGCCCGGTCG GCACCAG-TTGCGTGAGCGGAAAGATGGCCGCTTCCCGGCCC-TGCTGCAGGGAGC TCAAAATGGAGGACGCG-GCGCTCGGGAGAGCGGGCGGGTGAGTCACCCAC-ACA AAGGAAAAGGGCCTTTCCGTCCTCAGCCGTC-GCTTCATGTGACTCCACGGAGTAC CGGGCGC-CGTCCAGGCACCTCGATTAGTTCGCTTTTG-GAGTACGTCGTCTTTAGG TTGGGGGGAGGGGTTT-TATGCGATGGAGTTTCCCCACACTGAGTGGGTGGA-GAC TGAAGTTAGGCCAGCTTGGCACTTGATGT-AATTCTCCTTGGAATTTGCCCTTTTTG AGTTTG-GATCTTGGTTCATTCTCAAGCCTCAGACAGTGGTT-CAAAGTTTTTTTCTT CCATTTCAG). In some embodiments, the intron is 85%, 86%, 87%, 88%, 89%, 90%, 91%, 92%, 93%, 94%, 95%, 96%, 97%, 98%, 99% or 100% identical, or is within a range defined by any two of the aforementioned percentages, to a sequence of SEQ ID NO: 2.

In some embodiments, the transposase region further comprises a PiggyBac transposase 5′ catalytic region+stop codon comprising a nucleic acid sequence of SEQ ID NO: 3: (GTGCTGAAGAACTCCCGGTCCAGACCTGTG-GGCACCAGCATGTTCTGCTTCGAC GGCCCTCTG-ACCCTGGTGTCCTACAAGCCCAAGCCCGCCAA- GATGGTGTACCTGC TGAGCAGCTGTGACGAGGAC-GCCAGCATCAACGAGAGCACCGGCAAGCCCCAG ATGGTCATGTACTACAACCAGACCAAGGGCGGC-GTGGACACCCTGGACCAGATG TGCAGCGTGATGA-CATGCAGCAGAAAGACCAACCGGTGGCC-CATGGCCCTGCTG TACGGCATGATCAATATCGCC-TGCATCAACAGCTTCATCATCTACTCCCACAACG TGTCCAGCAAGGGCGAGAAGGTGCAGAGCCG-GAAGAAATTCATGCGGAACCTGT ACATGAGCCT-GACCTCCAGCTTCATGAGAAAGCGGCTGGAAG-CCCCCACCCTGA AGAGATACCTGCGGGACAA-CATCAGCAACATCCTGCCCAACGAGGTGCCCGGCA CCAGCGACGATAGCACAGAGGAACCCGTGAT-GAAGAAGCGGACCTACTGCACCT ACTGTCCCT-CTAAAATCCGGCGGAAGGCCAACGCCAGCTG-CAAAAAGTGCAAGA AAGTGATCTGCCGCGA-GCACAACATCGATATGTGCCAGAGCTGCTTCTGA). In some embodiments, the transposase catalytic region+stop codon is 85%, 86%, 87%, 88%, 89%, 90%, 91%, 92%, 93%, 94%, 95%, 96%, 97%, 98%, 99% or 100% identical, or is within a range defined by any two of the aforementioned percentages, to a sequence of SEQ ID NO: 3.

In some embodiments, the transposase region further comprises a promoter (in this example, an SV40 late poly(A) promoter) comprising a nucleic acid sequence of SEQ ID NO: 4: (GCTTTATTTGTGAAATTTGTGATGCTAT-TGCTTTATTTGTAACCATTATAAGCTGC AATAAA-CAAGTTAACAACAACAATTGCATTCATTTTATGT-TTCAGGTTCAGGGGG AGATGTGGGAGGTTTTT-TAAAGC). In some embodiments, the promoter is 85%, 86%, 87%, 88%, 89%, 90%, 91%, 92%, 93%, 94%, 95%, 96%, 97%, 98%, 99% or 100% identical, or is within a range defined by any two of the aforementioned percentages, to a sequence of SEQ ID NO: 4.

Thus, in some embodiments, the transposase region comprises a nucleic acid sequence comprising, from 5′ to 3′, a transposase catalytic region, an intron region, a transposase catalytic region+stop codon, or a promoter (SEQ ID NOs: 1-4), or any combination or variation thereof. Thus, in this example, the intron is inserted within the PB transposase, and the transposase is followed by the SV40 poly(A) region.

Furthermore, in some embodiments, the vector may comprise a transposon region comprising a 5′ terminal repeat (5′TR) comprising a nucleic acid sequence of SEQ ID NO: 5: (TTAACCCTAGAAAGATAATCATATTGTGACGT-ACGTTAAAGATAATCATGCGTA AAATTGACG-CATGTGTTTTATCGGTCTGTATATCGAGGTTTATTT-ATTAATTTGAA TAGATATTAAGTTTTATTATATTTA-CACTTACATACTAATAATAAATTCAACAAA CAAT-TTATTTATGTTTATTTATTTATTAAAAAAAAAACAA-AAACTCAAAATTTCTTC TATAAAGTAACAAAA-CTTTTA). In some embodiments, the 5′TR is 85%, 86%, 87%, 88%, 89%, 90%, 91%, 92%, 93%, 94%, 95%, 96%, 97%, 98%, 99% or 100% identical, or is within a range defined by any two of the aforementioned percentages, to a sequence of SEQ ID NO: 5.

In some embodiments, the transposon region further comprises a first core or insulator region comprising a nucleic acid sequence as set forth in SEQ ID NO: 6: (GAGGGACAGCCCCCCCCCAAAGCCCCCAGG-GATGTAATTACGTCCCTCCCCCGC TAGGGGGCAGC-AGCGAGCCGCCCGGGGCTCCGCTCCGGTCCGGCG-CTCCCCCCG CATCCCCGAGCCGGCAGCGTGCGG-GGACAGCCCGGGCACGGGGAAGGTGCAC GGG-ATCGCTTTCCTCTGAACGCTTCTCGCTGCTCTTT-GAGCCTGCAGACACCTGG GGGGATACGGG-GAAAAGGCTCGCGA). In some embodiments, the first core or insulator region is 85%, 86%, 87%, 88%, 89%, 90%, 91%, 92%, 93%, 94%, 95%, 96%, 97%, 98%, 99% or 100% identical, or is within a range defined by any two of the aforementioned percentages, to a sequence of SEQ ID NO: 6.

In some embodiments, the transposon region further comprises a promoter (in this example, an EF1α) promoter comprising a nucleic acid sequence as set forth in SEQ ID NO: 7: (GGATCTGCGATCGCTCCGGTGCC-CGTCAGTGGGCAGAGCGCACATCGCCCACAG TCCCCGAGAAGTTGGGGGGGAGGGGTCGGCAATT-GAACCGGTGCCTAGAGAAGGT GGCGCGGGG-TAAACTGGGAAAGTGATGTCGTGTACTGGCTC-CGCCTTTTTCCCGA GGGTGGGGGAGAACCGT-ATATAAGTGCAGTAGTCGCCGTGAACGTTCTTT-TTCGC AACGGGTTTGCCGCCAGAACACAGCTG). In some embodiments, the promoter is 85%, 86%, 87%, 88%, 89%, 90%, 91%, 92%, 93%, 94%, 95%, 96%, 97%, 98%, 99% or 100% identical, or is within a range defined by any two of the aforementioned percentages, to a sequence of SEQ ID NO: 7.

In some embodiments, the transposon region further comprises a gene of interest (GOI; in this example, eGFP), which may be flanked by enzymatic cut sites, such as NheI or BamHI sites, comprising a nucleic acid sequence as set forth in SEQ ID NO: 8: (GCTAGCATGCCCGCCATGAA-GATCGAGTGCCGCATCACCGGCACCCTGAACGGC GTGGAGTTCGAGCTGGTGGGCGGCGGAGAG-GGCACCCCCGAGCAGGGCCGCATG ACCAACAA-GATGAAGAGCACCAAAGGCGCCCTGACCTTCA-GCCCCTACCTGCTG AGCCACGTGATGGGC-TACGGCTTCTACCACTTCGGCACCTACCCCAG-CGGCTACG AGAACCCCTTCCTGCACGCCAT-CAACAACGGCGGCTACACCAACACCCGCATCG AGAAGTACGAGGACGGCGGCGTGCTGCACGT-GAGCTTCAGCTACCGCTACGAGG CCGGCCGCGT-GATCGGCGACTTCAAGGTGGTGGGCACCGGC-TTCCCCGAGGACAGCGTGATCTTCACCGACAAGAT-CATCCGCAGCAACGCCACCGTGGAGCACCTGC ACCCCATGGGCGATAACGTGCTGGTGGGCAGC-TTCGCCCGCACCTTCAGCCTGCG CGACGGCGGC-TACTACAGCTTCGTGGTGGACAGCCACATGCACTT-CAAGAGCGC CATCCACCCCAGCATCCTGCAGA-ACGGGGGCCCCATGTTCGCCTTCCGCCGCGTG GAGGAGCTGCACAGCAACACCGAGCTGGG-CATCGTGGAGTACCAGCACGCCTTC AAGACCCC-CATCGCCTTCGCCGGATCC; the enzymatic cut sites are underlined in this sequence). In some embodiments, the GOI is 85%, 86%, 87%, 88%, 89%, 90%, 91%, 92%, 93%, 94%, 95%, 96%, 97%, 98%, 99% or 100% identical, or is within a range defined by any two of the aforementioned percentages, to a sequence of SEQ ID NO: 8.

In some embodiments, the transposon region further comprises a T2A region comprising a nucleic acid sequence as set forth in SEQ ID NO: 9: (GGCGGCG-GAGAGGGCAGAGGAAGTCTTCTAA-CATGCGGTGACGTGGAGGAGAA TCCCGGCCCTAGG). In some embodiments, the T2A region is 85%, 86%, 87%, 88%, 89%, 90%, 91%, 92%, 93%, 94%, 95%, 96%, 97%, 98%, 99% or 100% identical, or is within a range defined by any two of the aforementioned percentages, to a sequence of SEQ ID NO: 9.

In some embodiments, the transposon region further comprises a drug selection gene (in this example a dihydro-folate reductase double mutant DHFRdm) comprising a nucleic acid sequence as set forth in SEQ ID NO: 10:

```
(ATGGTTGGTTCGCTAAACTGCATCGTCGCTGTGTCCCAGAACATGGGCA

TCGGCAAGAACGGGGACTTCCCCTGGCCACCGCTCAGGAATGAATCCAGA

TATTTCCAGAGAATGACCACAACCTCTTCAGTAGAAGGTAAACAGAATCT

GGTGATTATGGGTAAGAAGACCTGGTTCTCCATTCCTGAGAAGAATCGAC

CTTTAAAGGGTAGAATTAATTTAGTTCTCAGCAGAGAACTCAAGGAACCT

CCACAAGGAGCTCATTTTCTTTCCAGAAGTCTAGATGATGCCTTAAAACT

TACTGAACAACCAGAATTAGCAAATAAAGTAGACATGGTCTGGATAGTTG

GTGGCAGTTCTGTTTATAAGGAAGCCATGAATCACCCAGGCCATCTTAAA

CTATTTGTGACAAGGATCATGCAAGACTTTGAAAGTGACACGTTTTTTCC

AGAAATTGATTTGGAGAAATATAAACTTCTGCCAGAATACCCAGGTGTTC

TCTCTGATGTCCAGGAGGAGAAAGGCATTAAGTACAAATTTGAAGTATAT

GAGAAGAATGATTAAGGTACCGCGGCCGC;
```
enzymatic cut sites Acc65I and NotI are underlined). In some embodiments, the drug selection gene includes a stop codon. In some embodiments, the drug selection gene is 85%, 86%, 87%, 88%, 89%, 90%, 91%, 92%, 93%, 94%, 95%, 96%, 97%, 98%, 99% or 100% identical, or is within a range defined by any two of the aforementioned percent-ages, to a sequence of SEQ ID NO: 10.

In some embodiments, the transposon region further comprises a RBG poly(A) region comprising a nucleic acid sequence as set forth in SEQ ID NO: 11: (TTTTCCCTCTGCCAAAAATTATGGGGACATCAT-GAAGCCCCTTGAGCATCTGACT TCTGGCTAAT-AAAGGAAATTTATTTTCATTGCAATAGTGTGTTG-GAATTTTTTGTG TCTCTCACTCGGAAGGACAT-AAGG). In some embodiments, the RBG poly(A) region is 85%, 86%, 87%, 88%, 89%, 90%, 91%, 92%, 93%, 94%, 95%, 96%, 97%, 98%, 99% or 100% identical, or is within a range defined by any two of the aforementioned percent-ages, to a sequence of SEQ ID NO: 11.

In some embodiments, the transposon region further comprises a second core or insulator region comprising a nucleic acid sequence as set forth in SEQ ID NO: 12: (ATGGCTAGATCTTTTTCCCCGTATCCCCCCAGGTG-TCTGCAGGCTCAAAGAGCAG CGAGAAGCGTT-CAGAGGAAAGCGATCCCGTGCCACCTTCCCC-GTGCCCGGGCTG TCCCCGCACGCTGCCGGCTC-GGGGATGCGGGGGGGAGCGCCGGACCGGAGCGGAG CCCCGGGCGGCTCGCTGCTGCCCCCTAGCGGGG-GAGGGACGTAATTACATCCCT GGGGGCTTT-GGGGGGGGGCTGTCCCT). In some embodiments, the second core or insulator region is 85%, 86%, 87%, 88%, 89%, 90%, 91%, 92%, 93%, 94%, 95%, 96%, 97%, 98%, 99% or 100% identical, or is within a range defined by any two of the aforementioned percentages, to a sequence of SEQ ID NO: 12.

In some embodiments, the transposon region further comprises a 3' terminal repeat (3'TR) region comprising a nucleic acid sequence as set forth in SEQ ID NO: 13: (GATATCTATAACAAGAAAATATATATATAATAAGT-TATCACGTAAGTAGAACAT GAAATAACAATATAAT-TATCGTATGAGTTAAATCTTAAAAGTCACGTAAAA-GAT AATCATGCGTCATTTTGACTCACGCGG-TCGTTATAGTTCAAAATCAGTGACACTT ACCGCAT-TGACAAGCACGCCTCACGGGAGCTCCAAGCGG-CGACTGAGATGTCCT AAATGCACAGCGACGGAT-TCGCGCTATTTAGAAAGAGAGAGCAATATTT- CAAGA ATGCATGCGTCAATTTTACGCAGAC-TATCTTTCTAGGGTTAA). In some embodiments, the 3'TR is 85%, 86%, 87%, 88%, 89%, 90%, 91%, 92%, 93%, 94%, 95%, 96%, 97%, 98%, 99% or 100% identical, or is within a range defined by any two of the aforementioned percentages, to a sequence of SEQ ID NO: 13.

Thus, in some embodiments, the transposon region comprises a nucleic acid sequence comprising, from 5' to 3', a 5' terminal repeat, a first core or insulator region, a promoter region, a gene of interest, a T2A region, a drug selection gene, a RBG poly(A) region, a second core or insulator region, or a 3' terminal repeat, or any combination or variation thereof (SEQ ID NOs: 5-13). In some embodiments, the 3' terminal repeat is contained within the intron which is a transposase.

In some embodiments, the vector further comprises additional regions and components for gene delivery. Thus, for example, the vector may further comprise (listed in order following the 3' terminal repeat of the transposon region): a TRPA terminator region, an R6K mini origin region, an RNA-out region, a CMV enhancer, a CMV core promoter, a suicide gene, or a T2A region, or any combination or variation thereof.

More specifically, in some embodiments, the vector may comprise a TRPA terminator region comprising a nucleic acid sequence as set forth in SEQ ID NO: 14: (GTCGACCCGCCTAATGAGCCGCCTAATGAGCG-GGCTTTTTTTT; underlined portion is an enzymatic cut site SalI). In some embodiments, the TRPA terminator is 85%, 86%, 87%, 88%, 89%, 90%, 91%, 92%, 93%, 94%, 95%, 96%, 97%, 98%, 99% or 100% identical, or is within a range defined by any two of the aforementioned percentages, to a sequence of SEQ ID NO: 14.

In some embodiments, the vector may additionally comprise an R6K mini origin region comprising a nucleic acid sequence as set forth in SEQ ID NO: 15: (GGCTTGTTGTCCACAACCGTTAAACCTTAAAAG-CTTTAAAAGCCTTATATATTCT TTTTTTTCTTATA-AAACTTAAAACCTTAGAGGCTATTTAAGTTGCT-GATTTATATT AATTTTATTGTTCAAACATGAGAGCT-TAGTACGTGAAACATGAGAGCTTAGTACG TTAGC-CATGAGAGCTTAGTACGTTAGCCATGAGGGTTTAG-TTCGTTAAACATGAG AGCTTAGTACGTTAAACAT-GAGAGCTTAGTACGTACTATCAACAGGTTGAAC-TGC TGATC). In some embodiments, the R6K mini origin is 85%, 86%, 87%, 88%, 89%, 90%, 91%, 92%, 93%, 94%, 95%, 96%, 97%, 98%, 99% or 100% identical, or is within a range defined by any two of the aforementioned percentages, to a sequence of SEQ ID NO: 15.

In some embodiments, the vector may additionally comprise an RNA-out region comprising a nucleic acid sequence as set forth in SEQ ID NO: 16: (CACGTTGTGGTAGAAT-TGGTAAAGAGAGTCGTGTAAAATATCGAGTTCGCA-CAT CTTGTTGTCTGATTATTGATTTTTGGCGAAAC-CATTTGATCATATGACAAGATGTG TATCTACCT-TAACTTAATGATTTTGATAAAAATCATTAGG). In some embodiments, the RNA-out is 85%, 86%, 87%, 88%, 89%, 90%, 91%, 92%, 93%, 94%, 95%, 96%, 97%, 98%, 99% or 100% identical, or is within a range defined by any two of the aforementioned percentages, to a sequence of SEQ ID NO: 16.

In some embodiments, the vector may additionally comprise a CMV enhancer comprising a nucleic acid sequence as set forth in SEQ ID NO: 17: (CTAGTTAT-TAATAGTAATCAATTACGGGGTCATTAGTTCAT-AGCCCATATATGGA GTTCCGCGTTACATAACT-TACGGTAAATGGCCCGCCTGGCTGACCGCCCAAC- GAC CCCCGCCCATTGACGTCAATAATGACGTAT-GTTCCCATAGTAACGCCAATAGGGA CTTTCCAT-TGACGTCAATGGGTGGAGTATTTACGGTAAACT-GCCCACTTGGCAGT ACATCAAGTGTATCATATGC-CAAGTACGCCCCCTATTGACGTCAATGACGGTAAA TGGCCCGCCTGGCATTATGCCCAGTACATGACCT-TATGGGACTTTCCTACTTGGC AGTACATCTACGT-ATTAGTCATCGCTATTACCATGGTGATGCGGTTT-TGGCAGTA CATCAATGGGCGTGGATAGCGGTT-TGACTCACGGGGATTTCCAAGTCTCCACCCC ATTGACGTCAATGGGAGTTTGTTTTGG). In some embodiments, the CMV enhancer is 85%, 86%, 87%, 88%, 89%, 90%, 91%, 92%, 93%, 94%, 95%, 96%, 97%, 98%, 99% or 100% identical, or is within a range defined by any two of the aforementioned percentages, to a sequence of SEQ ID NO: 17.

In some embodiments, the vector may additionally comprise a CMV core promoter comprising a nucleic acid sequence as set forth in SEQ ID NO: 18: (CACCAAAAT-CAACGGGACTTTCCAAAATGTCGTAACAACTCC-GCCCCATTGACG CAAATGGGCGGTAGGCGTGT-ACGGTGGGAGGTCTATATAAGCAGAGCTCGTTTA GTGAACCGTCAGATCGCCTGGAGACGCCATC-CACGCTGTTTTGACCTCCATAGA). In some embodiments, the CMV core promoter is 85%, 86%, 87%, 88%, 89%, 90%, 91%, 92%, 93%, 94%, 95%, 96%, 97%, 98%, 99% or 100% identical, or is within a range defined by any two of the aforementioned percentages, to a sequence of SEQ ID NO: 18.

In some embodiments, the vector may additionally comprise a suicide gene comprising a nucleic acid sequence as set forth in SEQ ID NO: 19: (ATGCCCACGC-TACTGCGGGTTTATATAGACGGTCCCCACGG-GATGGGGAAAACC ACCACCACGCAACTGCTG-GTGGCCCTGGGTTCGCGCGACGATATCGTC-TACGTAC CCGAGCCGATGACTTACTGGCGGGT-GCTGGGGGCTTCCGAGACAATCGCGAACA TCTA-CACCACACAACACCGCCTCGACCAGGGTGAGA-TATCGGCCGGGGACGCGG CGGTGGTAATGACA-AGCGCCCAGATAACAATGGGCATGCCTTATGCCG-TGACCG ACGCCGTTCTGGCTCCTCATATCGGGGGG-GAGGCTGGGAGCTCACATGCCCCGCC CCCGGC-CCTCACCATCTTCCTCGACCGCCATCCCATCGCCTT-CATGCTGTGCTACC CGGCCGCGCGGTACCT-TATGGGCAGCATGACCCCCCAGGCCGTGCTG-GCGTTCGT GGCCCTCATCCCGCCGACCTTG-CCCGGCACCAACATCGTGCTTGGGGCCCTTCCG GAGGACAGACACATCGACCGCCTGGCCAAACG-CCAGCGCCCCGGCGAGCGGCTG GACCTGGC-TATGCTGGCTGCGATTCGCCGCGTTTACGGGC-TACTTGCCAATACGG TGCGGTATCTGCAGTGCG-GCGGGTCGTGGCGGGAGGACTGGGGACAGCT-TTCGG GGACGGCCGTGCCGCCCCAGGGTGCCGA-GCCCCAGAGCAACGCGGGCCCACGAC CCCATATC-GGGGACACGTTATTTACCCTGTTTCGGGCCCC-CGAGTTGCTGGCCCC CAACGGCGACCTGTATAAC-GTGTTTGCCTGGGCCTTGGACGTCTTGGCCAAA-CGC CTCCGTTCCATGCACGTCTTTATCCTGGAT-TACGACCAATCGCCCGCCGGCTGCC GGGACGCC-CTGCTGCAACTTACCTCCGGGATGGTCCAGACC-CACGTCACCACCCC CGGCTCCATACCGACGA-TATGCGACCTGGCGCGCACGTTTGCCCGG-GAGATGGG GGAGGCTAAC). In some embodiments, the suicide gene is 85%, 86%, 87%, 88%, 89%, 90%, 91%, 92%, 93%, 94%, 95%, 96%, 97%, 98%, 99% or 100% identical, or is within a range defined by any two of the aforementioned percentages, to a sequence of SEQ ID NO: 19.

In some embodiments, the vector may additionally comprise a T2A region comprising a nucleic acid sequence as set forth in SEQ ID NO: 20: (GGCGGCG-GAGAGGGCAGAGGAAGTCTTCTAACATGCG-GTGACGTGGAGGAGAA TCCCGGCCCT). In some embodiments, the T2A is 85%, 86%, 87%, 88%, 89%, 90%, 91%, 92%, 93%, 94%, 95%, 96%, 97%, 98%, 99% or 100% identical, or is within a range defined by any two of the aforementioned percentages, to a sequence of SEQ ID NO: 20.

Thus, the vector may include, from 5' to 3', a transposase region as described herein, a transposon region as described herein, and additional components as described herein, including the nucleic acid sequences as set forth in SEQ ID NOs: 1-20.

The elements described herein, including the sequences described by SEQ ID NOs: 1-20, may be included in a vector for gene delivery in a self-inactivating transposase delivery system. Any suitable vector may be used that is suitable for gene delivery, including, for example plasmid or viral vectors, such as adeno-associated virus (AAV), lentivirus, adenovirus, or other viral vector types, or combinations thereof.

A "promoter" is a nucleotide sequence that directs the transcription of a structural gene. In some alternatives, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., Mol. Endocrinol. 7:551 (1993); incorporated by reference in its entirety), cyclic AMP response elements (CREs), serum response elements (SREs; Treisman, Seminars in Cancer Biol. 1:47 (1990); incorporated by reference in its entirety), glucocorticoid response elements (GREs), and binding sites for other transcription factors, such as CRE/ATF (O'Reilly et al., J. Biol. Chem. 267:19938 (1992); incorporated by reference in its entirety), AP2 (Ye et al., J. Biol. Chem. 269:25728 (1994); incorporated by reference in its entirety), SP1, cAMP response element binding protein (CREB; Loeken, Gene Expr. 3:253 (1993); incorporated by reference in its entirety) and octamer factors (see, in general, Watson et al., eds., Molecular Biology of the Gene, 4th ed. (The Benjamin/Cummings Publishing Company, Inc. 1987; incorporated by reference in its entirety)), and Lemaigre and Rousseau, Biochem. J. 303:1 (1994); incorporated by reference in its entirety). As used herein, a promoter can be constitutively active, repressible, or inducible. If a promoter is an inducible promoter, then the rate of transcription increases in response to an inducing agent. In contrast, the rate of transcription is not regulated by an inducing agent if the promoter is a constitutive promoter. Repressible promoters are also known. In some alternatives, a gene delivery vector is provided. In some alternatives, the gene delivery vector comprises a promoter sequence. In some embodiments, the promoter sequence is an elongation factor (such as EF1α) promoter.

A marker is a gene introduced into a vector or a cell that confers a trait for artificial selection. A marker can be a screenable marker to allow a researcher to distinguish between wanted and unwanted cells, or to enrich for a specific cell type. In some alternatives, a gene delivery vector is provided. In some alternatives, the gene delivery vector comprises a marker. In some embodiments, the marker is a fluorescent protein, such as a cyan florescent protein (CFP), green florescent protein (GFP), orange florescent protein (OFP), red florescent protein (RFP), or yellow florescent protein (YFP).

"Methotrexate" (MTX), has its plain and ordinary meaning when read in light of the specification, and may include but is not limited to, for example, an antimetabolite and antifolate drug. It acts by inhibiting the metabolism of folic acid. In some alternatives, a method of generating engineered multiplexed T-cells for adoptive T-cell immunotherapy is provided. In the broadest sense, the method can comprise providing the gene delivery vector of any of the alternatives described herein, selecting the cells comprising the gene delivery vector, wherein the selecting comprises adding a selection reagent. In some alternatives described herein, the selection reagent comprises an agent for selection. In some alternatives, the selection reagent is MTX.

A drug selection gene refers to a gene that confers some selective properties to a cell when the cell is contacted with a drug. In some embodiments, the drug selection gene is dihydrofolate reductase (DHFR). DHFR is an enzyme that reduces dihydrofolic acid to tetrahydrofolic acid, using NADPH as electron donor, which can be converted to the kinds of tetrahydrofolate cofactors used in 1-carbon transfer chemistry. In some alternatives described herein, a gene delivery vector is provided. In some alternatives, the gene delivery vector includes a nucleic acid sequence encoding for a double mutant of dihydrofolate reductase. Cells without DHFRdm are susceptible to inhibition of cellular replication via methotrexate addition. In some embodiments, a drug selection gene encodes a dihydrofolate reductase (DHFR), DHFR double mutant (DHFRdm), hygromycin-B phosphotransferase (hph), aminoglycoside phosphotransferase, β-lactamase, chloramphenicol acetyltransferase (CAT), adenosine deaminase (ADA), thymidine kinase (TK), lacz (encoding (β-galactosidase), bleomycin resistance, metallothionein, or xanthine guanine phosphoribosyltransferase (XGPRT), or any derivative or analogue thereof.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein can also comprise non-peptide components, such as carbohydrate groups. Carbohydrates and other non-peptide substituents can be added to a protein by the cell in which the protein is produced and will vary with the type of cell. Proteins are defined herein in terms of their amino acid backbone structures; substituents such as carbohydrate groups are generally not specified but can be present nonetheless. In some alternatives, a gene delivery vector is provided. In some alternatives, the gene delivery vector further comprises a sequence for at least one protein.

An "antibody" as described herein refers to a large Y-shape protein produced by plasma cells that is used by the immune system to identify and neutralize foreign objects such as bacteria and viruses. The antibody protein can comprise four polypeptide chains; two identical heavy chains and two identical light chains connected by disulfide bonds. Each chain is composed of structural domains called immunoglobulin domains. These domains can contain about 70-110 amino acids and are classified into different categories according to their size and function. In some alternatives, a gene delivery vector is provided. In some alternatives, the gene delivery vector further comprises a sequence for at least one protein. In some alternatives, the gene delivery vector can comprise a sequence for an antibody or a portion thereof, which may be humanized.

A "chimeric antigen receptor" (CAR), also known as chimeric T-cell receptors, refers to artificial T-cell receptors that are engineered receptors, which graft an arbitrary specificity onto an immune effector cell. These receptors can be used to graft the specificity of a monoclonal antibody onto a T-cell, for example; with transfer of their coding sequence facilitated by retroviral vectors, or any other suitable gene delivery system. The structure of the CAR can comprise single-chain variable fragments (scFv) derived from monoclonal antibodies, fused to CD3-zeta transmembrane and endodomain. Such molecules result in the transmission of a zeta signal in response to recognition by the scFv of its target. Some alternatives utilize a gene delivery vector having a self-inactivating transposase system. In some alternatives, the gene delivery vector further comprises a sequence for at least one protein. In some alternatives, the protein is a chimeric antigen receptor. Chimeric receptor can also be referred to as artificial T cell receptors, chimeric T cell receptors, chimeric immunoreceptors, and/or CARs. These CARs are engineered receptors that can graft an arbitrary specificity onto an immune receptor cell. CARs may include the antibody or antibody fragment, spacer, signaling domain, and/or transmembrane region. However, due to the surprising effects of modifying the different components or domains of the CAR, such as the epitope binding region (for example, antibody fragment, scFv, or portion thereof), spacer, transmembrane domain, and/or signaling domain), the components of the CAR are described herein in some contexts to include these features as independent elements. The variation of the different elements of the CAR can, for example, lead to stronger binding affinity for a specific epitope.

Artificial T-cell receptors, or CARS, can be used as a therapy for cancer or viral infection using a technique called adoptive cell transfer. T-cells are removed from a subject and modified so that they express receptors specific for a molecule displayed on a cancer cell or virus, or virus-infected cell. The genetically engineered T-cells, which can then recognize and kill the cancer cells or the virus infected cells or promote clearance of the virus, are reintroduced into the subject In some alternatives, the gene delivery vector can comprise a sequence for a chimeric antigen receptor. In some alternatives, a method of generating engineered multiplexed T-cells for adoptive T-cell immunotherapy is provided. In the broadest sense the method can comprise providing the gene delivery vector of any one of the alternatives described herein, introducing the gene delivery vector into a T-cell, selecting the cells comprising the gene delivery vector, wherein selecting comprises isolating the T-cells expressing a phenotype under selective pressure.

T-cell co-stimulation is desired for development of an effective immune response and this event occurs during the activation of lymphocytes. A co-stimulatory signal, is antigen non-specific and is provided by the interaction between co-stimulatory molecules expressed on the membrane of the antigen bearing cell and the T-cell. Co-stimulatory molecules can include but are not limited to CD28, CD80, and CD86. In some alternatives, a method for generating engineered multiplexed T-cell for adoptive T-cell immunotherapy is provided. In some alternatives, the T-cell is a chimeric antigen receptor bearing T-cell. In some alternatives, the chimeric antigen receptor bearing T-cell is engineered to express co-stimulatory ligands. In some alternatives, methods are provided for treating, inhibiting, or ameliorating cancer or a viral infection in a subject. In the broadest sense, the method can comprise administering to the subject a T-cell of any of the alternatives described herein. In some of these alternatives, the subject is an animal, such as domestic livestock or a companion animal and on other alternatives, the subject is a human. In some of these alternatives, the chimeric antigen bearing T-cell is engineered to express a co-stimulatory molecule. In some alternatives, the gene delivery vector comprises a sequence for at least one co-stimulatory molecule. In some alternatives, the gene delivery vector is at least 1 kB to 20 kB.

A peptide or polypeptide encoded by a non-host DNA molecule is a "heterologous" peptide or polypeptide.

An "integrated genetic element" is a segment of DNA that has been incorporated into a chromosome of a host cell after that element is introduced into the cell through human manipulation. Within the present alternatives, integrated genetic elements can be derived from vectors that are introduced into the cells by electroporation or other techniques. Integrated genetic elements are passed from the original host cell to its progeny. In some alternatives, the gene delivery vector is at least 1 kB to 20 kB.

As used herein, "nucleofection", refers to a transfection method of exogenous nucleic acid(s) into a host cell and is performed by electroporation. In some alternatives, a method of generating engineered multiplexed T-cells for adoptive T-cell immunotherapy is provided. In the broadest sense the method can comprise providing the gene delivery vector of any of the alternatives described herein, introducing the gene delivery vector into a T-cell, selecting the cells comprising the gene delivery vector, and isolating the T-cells expressing a phenotype under selective pressure.

"Host cell" or "cell" as described herein, is a cell that contains one or more nucleases, for example endonucleases, end-processing enzymes, and/or endonuclease/end-processing enzyme fusion proteins encompassed by the present alternatives or a vector encoding the same that supports the replication, and/or transcription or transcription and translation (expression) of one or more nucleases, for example endonucleases, end-processing enzymes, and/or endonuclease/end-processing enzyme fusion proteins. In some alternatives, host cells for use in the present alternatives can be eukaryotic cells. Host cells of the immune system can include T-cells. In some alternatives, a method of generating engineered multiplexed T-cells for adoptive T-cell immunotherapy is provided. In some alternatives, the method can comprise providing the gene delivery vector of any one of the alternatives described herein, introducing the gene delivery vector into a T-cell, selecting the cells comprising the gene delivery vector, and isolating the T-cells expressing a phenotype under selective pressure.

"Codon optimization" as described herein, refers to the design process of altering codons to codons known to increase maximum protein expression efficiency in a desired cell. In some alternatives, codon optimization is described, wherein codon optimization can be performed by using algorithms that are known to those skilled in the art to create synthetic genetic transcripts optimized for high protein yield. Programs containing algorithms for codon optimization are known to those skilled in the art. Programs can include, for example, OptimumGene™, GeneGPS® algorithms, etc. Additionally, synthetic codon optimized sequences can be obtained commercially for example from Integrated DNA Technologies and other commercially available DNA sequencing services. In some alternatives, a gene delivery vector having a self-inactivating transposase system is provided. In some alternatives, the gene delivery vectors having a gene of interest are codon optimized for expression in humans, a domestic animal, or a companion animal. In some alternatives, the genes are optimized to have selected codons specifically for maximal protein expression in human cells, which can increase the concentration of proteins or CARs of a T-cell.

Codon optimization can be performed to reduce the occurrence of secondary structure in a polynucleotide, as well. In some alternatives, codon optimization can also be performed to reduce the total GC/AT ratio. Strict codon optimization can also lead to unwanted secondary structure or an undesirable GC content that leads to secondary structure. As such, the secondary structures affect transcriptional efficiency. Programs such as GeneOptimizer can be used after codon usage optimization, for secondary structure avoidance and GC content optimization. These additional programs can be used for further optimization and troubleshooting after an initial codon optimization to limit secondary structures that may occur after the first round of optimization. Alternative programs for optimization are known to those skilled in the art. In some alternatives, a gene delivery vector having a self-inactivating transposase system provided. In some alternatives, the gene delivery vector comprises sequences that are codon optimized for expression in humans and/or to remove secondary structure and/or to reduce the total GC/AT ratio. In some alternatives, the sequences are optimized for secondary structure avoidance. In some alternatives, the sequences are optimized to reduce the total GC/AT ratio.

In some embodiments, the gene delivery vector comprises a suicide gene. A suicide gene is a nucleic acid sequence encoding a product that causes cell death by itself or in the presence of other compounds. In some embodiments, the suicide gene is thymidine kinase, referred to as SR39TK, and comprising a nucleic acid sequence as set forth in SEQ ID NO: 19. Thymidine kinase may be activated in the presence of an agent, such as ganciclovir, penciclovir, val-ganciclovir, acyclovir, or val-aciclovir. Examples of suicide gene/prodrug combinations which may be used are herpes simplex virus-thymidine kinase (HSV-tk) and ganciclovir, acyclovir; oxidoreductase and cycloheximide; cytosine deaminase and 5-fluorocytosine; thymidine kinase thymidilate kinase (Tdk::Tmk) and AZT; and deoxycytidine kinase and cytosine arabinoside; or derivatives and analogues of any of the aforementioned genes.

In some alternatives, a method of generating engineered multiplexed T-cells for adoptive T-cell immunotherapy is provided. In the broadest sense, some of these methods comprise providing the gene delivery vector having a self-inactivating transposase system, as described in any one of the alternatives described herein, introducing the gene delivery vector into a T-cell, selecting the cells comprising the gene delivery vector, wherein selecting comprises adding a selection reagent, and isolating the T-cells expressing a phenotype under selective pressure. In some alternatives, the selection reagent is methotrexate (MTX).

Adoptive Immunotherapy for Cancer or Antiviral Therapy

Embodiments provided herein relate to methods of treating a subject. Accordingly, the compositions described herein may be used for therapeutic purposes. Advantageously, in some embodiments, the compositions provide for single delivery of a gene of interest to a subject in need thereof. Thus, in contrast to conventional delivery methods, wherein delivery is performed by electroporation of the transposon and the transposase separately, the compositions and methods provided herein allow delivery of a self-inactivation transposon in a single delivery system. For example, a transposon containing a self-inactivating transposase. Furthermore, the compositions and methods provided herein relate to a non-viral approach for stable introduction of genes.

The premise of adoptive immunotherapy for cancer is transferring a subject's own tumor-specific T-cells into patients to facilitate the destruction of malignant cells. T-cells can be genetically-engineered to recognize tumor-specific antigens and exert cytotoxic activity against cancer cells. A method of adoptive immunotherapy for cancer is to isolate patient T-cells and introduce tumor recognition capability by expressing chimeric antigen receptors (CARs), membrane proteins that contain an extracellular tumor-binding domain linked to an intracellular signaling domain via a transmembrane segment. "Adoptive immunotherapy" or "T-cell adoptive transfer" refers to use of T-cell based cytotoxic response to attack cancer cells or specific cell targets. T-cells that have a natural or genetically engineered reactivity to a patient's cancer can be generated in vitro and then transferred back into the subject in need. Without being limiting, an example of adoptive transfer can be achieved by removing T-cells from a subject that has cancer or a viral disease and these T-cells can be genetically engineered to express receptors specific for biomarkers found on a cancer cell or virus such that the genetically engineered T-cells attack the cancer cells or virus or virus infected cells once the genetically engineered T-cells are transferred back into the subject. In some alternatives, a method of generating engineered multiplexed T-cells for adoptive T-cell immunotherapy is provided. In some alternatives, methods of targeting malignant cells for destruction are provided. In some alternatives a method of treating, inhibiting, or ameliorating a cancer or a viral disease in a subject is provided. In some alternatives the method of treating, inhibiting, or ameliorating a cancer or a viral disease in a subject comprises administering to the subject engineered multiplexed T-cells for adoptive T-cell immunotherapy, as described herein. In some alternatives, the subject is human.

The co-integration of additional genes can further increase the anti-tumor or antiviral activity of CAR-expressing T-cells. Comprehensive T-cell activation requires, in addition to initial tumor or viral recognition and signal initiation by CAR, engagement of costimulatory and cytokine receptors, which may not be present within the immunosuppressive environment of the tumor or the viral infected subject. To address this immunosuppressive environment of the tumor, for example, expression of co-stimulatory ligands such as CD80 and 4-1BBL in engineered, CAR-expressing T-cells can result in greater T-cell expansion due to auto-co-stimulation compared to expression of co-stimulatory ligands on tumor cells. Another challenge in T-cell immunotherapy is cell survival after infusion into patients. Induced expression of anti-apoptotic proteins has been shown to improve in vivo survival of T-cells. Tumor homing and infiltration can be increased by introduction of chemokine receptors in engineered T-cells and this approach can be especially useful for tumors that express chemokines that are not normally recognized by T-cells. Finally, T-cells can be engineered to better resist the immunosuppressive tumor microenvironment or the immunocompromised virally infected subject through, for example, induced cytokine expression. Thus, methods to rapidly generate engineered T-cells expressing multiple transgenes are important and advantageous for clinical translation of T-cell immunotherapy. In some alternatives, methods of generating engineered multiplexed T-cells for adoptive T-cell immunotherapy are provided. In some alternatives, the T-cells express chimeric antigen receptors. In some alternatives, T-cells expressing chimeric antigen receptors are engineered to express co-stimulatory ligands. In some alternatives, the T-cells expressing chimeric antigen receptors express co-stimulatory ligands. In some alternatives the co-stimulatory ligands are CD80. In some alternatives, the co-stimulatory ligands are 4-1BBL.

Adoptive cell transfer can refer to the transfer of cells, immune-derived cells, back into the same patient or into a different recipient host. For isolation of immune cells for adoptive transfer, blood can be drawn into tubes containing anticoagulant and the PBM (buffy coat) cells are isolated, typically by density barrier centrifugation. In T-cell based therapies, the cells can be expanded in vitro using cell culture methods relying heavily on the immunomodulatory action of interleukin-2 and returned to the patient in large numbers intravenously in an activated state. Anti-CD3 antibody can be used to promote the proliferation of T-cells in culture. Research into interleukin-21 indicates that it can also play an important role in enhancing the efficacy of T-cell based therapies prepared in vitro. Cells used in adoptive cell transfer can be used to deliver genetically modified lymphocytes, using recombinant DNA technology to achieve any number of goals. In some alternatives described herein, adoptive cell transfer is used to transfer cells into a subject, wherein the cells are CAR expressing lymphocytes. In some alternatives, the CAR expressing lymphocytes are host cells in methods for generating engineered multiplexed T-cells for adoptive T-cell immunotherapy. In some alternatives, the method comprises providing the gene delivery vectors of the alternatives described herein having a self-inactivating transposase system, selecting the cells comprising the gene delivery vector, wherein selecting comprises adding a selection reagent, and isolating the T-cells expressing a phenotype under selective pressure. In some alternatives, the gene delivery vector comprises a sequence for a co-stimulatory ligand. In some alternatives, the gene delivery vector comprises a sequence for a chimeric antigen receptor. In some alternatives, the T-cell expresses a CAR. In some alternatives, the selection reagent is MTX.

By way of example and not of limitation, genetically engineered T-cells are created by infecting patient's cells with a transferring virus that contain a copy of a T-cell receptor (TCR) gene that is specialized to recognize, for example, tumor or viral antigens. It is important that the transferring virus is not able to reproduce within the cell however but should integrate into the human genome. This is beneficial as the new TCR gene remains stable in the T-cell. A patient's own T-cells are exposed to these transferring viruses and then are expanded non-specifically or stimulated using the genetically engineered TCR. The cells are then transferred back into the patient and are ready to mount an immune response against the tumor, virus, or viral infected cell. The use of adoptive cell transfer with genetically engineered T-cells is a promising new approach for the treatment of a variety of cancers or viral infections. In some alternatives, methods of adoptive immunotherapy for cancer are provided. In some alternatives, methods of adoptive immunotherapy for viral infections are provided.

The method of making genetically engineered T-cells by using a viral vector can have several drawbacks. Genetic modification of T-cells is typically accomplished using γ-retroviral or lentiviral vectors. While effective, drawbacks include cost of production, limited gene packaging capacity, and potential safety issues. Plasmids containing transposon systems such as Sleeping Beauty (SB) or piggyBac offer a non-viral approach for stably introducing genes into T-cells.

Recently, the piggyBac system was used to produce stably-transfected mammalian cells expressing multiple transgenes of interest by delivery of multiple transposons. The SB system, first reactivated for mammalian cell use by Ivics and coworkers, has been used as the gene delivery modality in clinical trials of T-cell immunotherapy. These transposase/transposon systems are useful for genetic engineering of cells as they efficiently insert foreign genetic material into cells of interest. The transposon and transposase are delivered separately due to safety reasons involving potential integration of transposase genes into the host cell. In some alternatives described herein, self-inactivating transposase systems are provided in a single gene delivery vector. Thus, the compositions, systems, and methods described herein relate to a single-component system where a two-component system would ordinarily be necessary, thereby simplifying use of the system and simultaneously reducing costs associated with its use. Although the description relates to and describes use of the compositions, systems, and methods in the engineering of immune cells, those of skill in the art will readily recognize that the self-inactivating transposase system described herein may be expanded for use into any genetic engineering application where integration of a gene into a host genome is preferred.

In some alternatives, methods of generating engineered multiplexed T-cells for adoptive T-cell immunotherapy are provided. In the broadest sense, the method can comprise providing the gene delivery vector of any of the alternatives described herein, introducing the gene delivery vector into a T-cell, selecting the cells comprising the gene delivery vector, wherein selecting comprises adding a selection reagent, and isolating the T-cells expressing a phenotype under selective pressure. In some alternatives, the T-cells are chimeric antigen receptor (CAR) expressing T-cells. In some alternatives, the selection reagent is MTX.

In some alternatives, methods of increasing protein production in a T-cell are provided. In the broadest sense, the method can comprise providing the gene delivery vector of any of the alternatives described herein, introducing the gene delivery vector into a T-cell, selecting the cells comprising the gene delivery vector, wherein selecting comprises adding a selection reagent, and isolating the T-cells expressing a phenotype under selective pressure. In some alternatives, the selection reagent is MTX. In some alternatives, the T-cells are chimeric antigen receptor (CAR) expressing T-cells.

A selection mechanism for rapid selection of engineered T-cells can also be employed. The double mutant of human dihydrofolate reductase (DHFRdm, with amino acid mutations L22F and F31S) exhibits a 15,000-fold reduced affinity for methotrexate, a potent inhibitor of DHFR that results in blockade of thymidylate and purine synthesis. Expression of DHFRdm in T-cells imparts MTX resistance without compromising proliferative ability, expression of T-cell markers, or cytolytic ability. Additional advantages of this selection system include availability of clinical grade MTX, the use of a non-genotoxic drug, and the small gene size of DHFRdm (561 bp). Therefore, MTX can be used as a selection mechanism to selectively amplify SB-transduced cells. In some alternatives, the vectors comprise a genetic sequence encoding a double mutant of human dihydrofolate reductase. In some alternatives, a selection method for rapid selection of engineered T-cells is provided. In some alternatives, the selection method comprises contacting engineered T-cells with clinical grade methotrexate. In some alternatives, the double mutant of human dihydrofolate reductase exhibits a 15,000 fold or about 15,000 fold reduced specificity for methotrexate. In some alternatives, methotrexate can be used to contact the T-cells for selectively amplifying cells transduced with vectors, wherein the vectors comprise a sequence for the double mutant of human dihydrofolate reductase. In some alternatives, the gene encoding the double mutant of human dihydrofolate reductase comprises the DNA sequence as set forth in SEQ ID NO: 10, or a nucleic acid sequence that is 85%, 86%, 87%, 88%, 89%, 90%, 91%, 92%, 93%, 94%, 95%, 96%, 97%, 98%, 99% or 100% identical, or is within a range defined by any two of the aforementioned percentages, to a sequence of SEQ ID NO: 10.

EXAMPLES

Example 1: Self-Inactivating Transposase System

The following example demonstrates the transient expression of a gene of interest (GOI) in a cell population at an early time point (day two) to show plasmid functionality. This example also demonstrates integrated expression of a GOI in a distinct cell population at later time points (days seven and fourteen) to show intron and transposase-integration functionalities. Finally, this example demonstrates drug selection against unintegrated cell population to show selection functionality.

Figure 5:
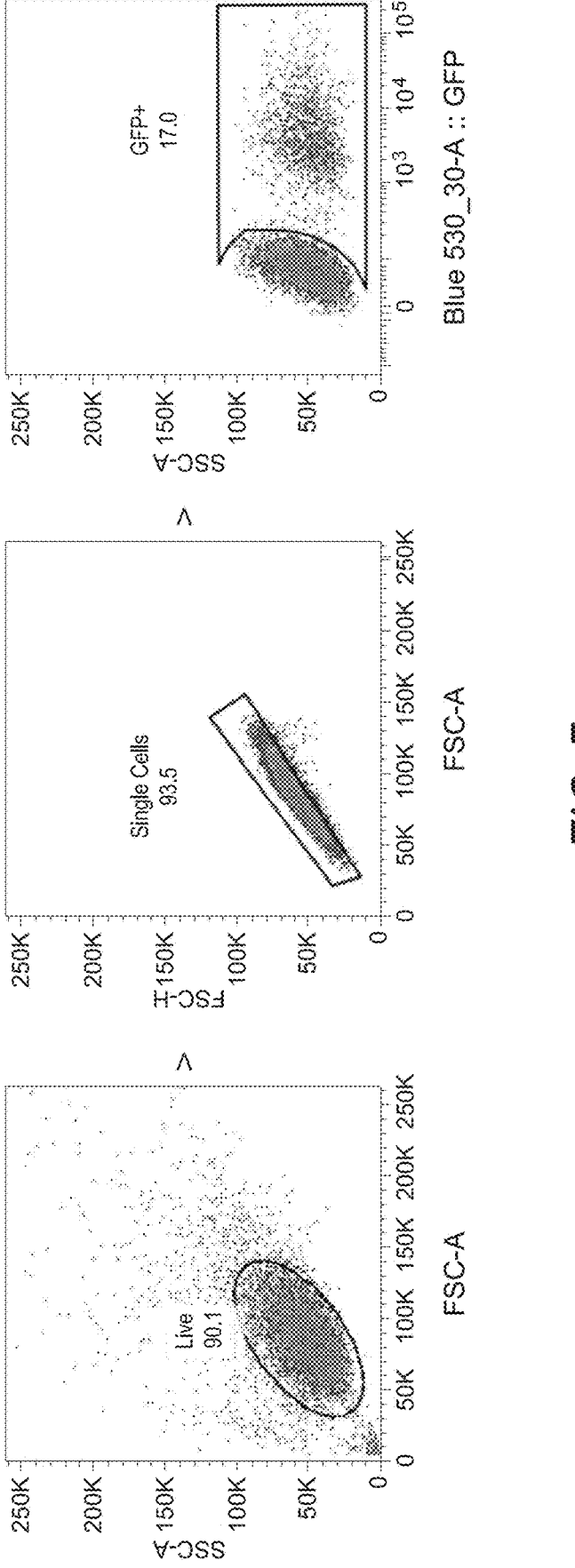
FIG. 5 depicts an exemplary gating strategy for experimental results of expression of GFP, including forward scatter gating (FSC) and side scatter gating (SSC) strategies. The examples depict FSC-A/SSC-A (Live)>FSC-A/FSC-H (Singlets)>Blue530:30/SSC-A (GFP-+).

Human suspension tumor cells (cell line K562, ATCC #CCL-243) were electroporated on day zero with a nanoplasmid construct, in various conditions containing a self-inactivating transposase and a GOI, green fluorescent protein (GFP) in this example, within a transposon. Control conditions included a non-electroporated sample, a no-DNA electroporated sample (Mock), and a control-GFP DNA electroporated sample. All cells were cultured in a plate for fourteen days, with methotrexate-mediated drug selection (+MTX) against unintegrated cell populations beginning on day one. Expression of the GOI was observed over the course over fourteen days via flow cytometric analysis of GFP expression, and time points were taken on days two, seven, and fourteen. Flow cytometry was performed on all samples to compare expression levels across conditions, and gating was drawn against the Mock sample. An example gating hierarchy is shown in FIG. 5.

Plasmid functionality was confirmed via data collected on day two. Intron and transposase functionalities were confirmed via data collected on days two, seven, and fourteen. Drug selection functionality was confirmed via data collected on days two, seven, and fourteen. Flow cytometry results are shown in FIGS. 6-8.

Figure 6:
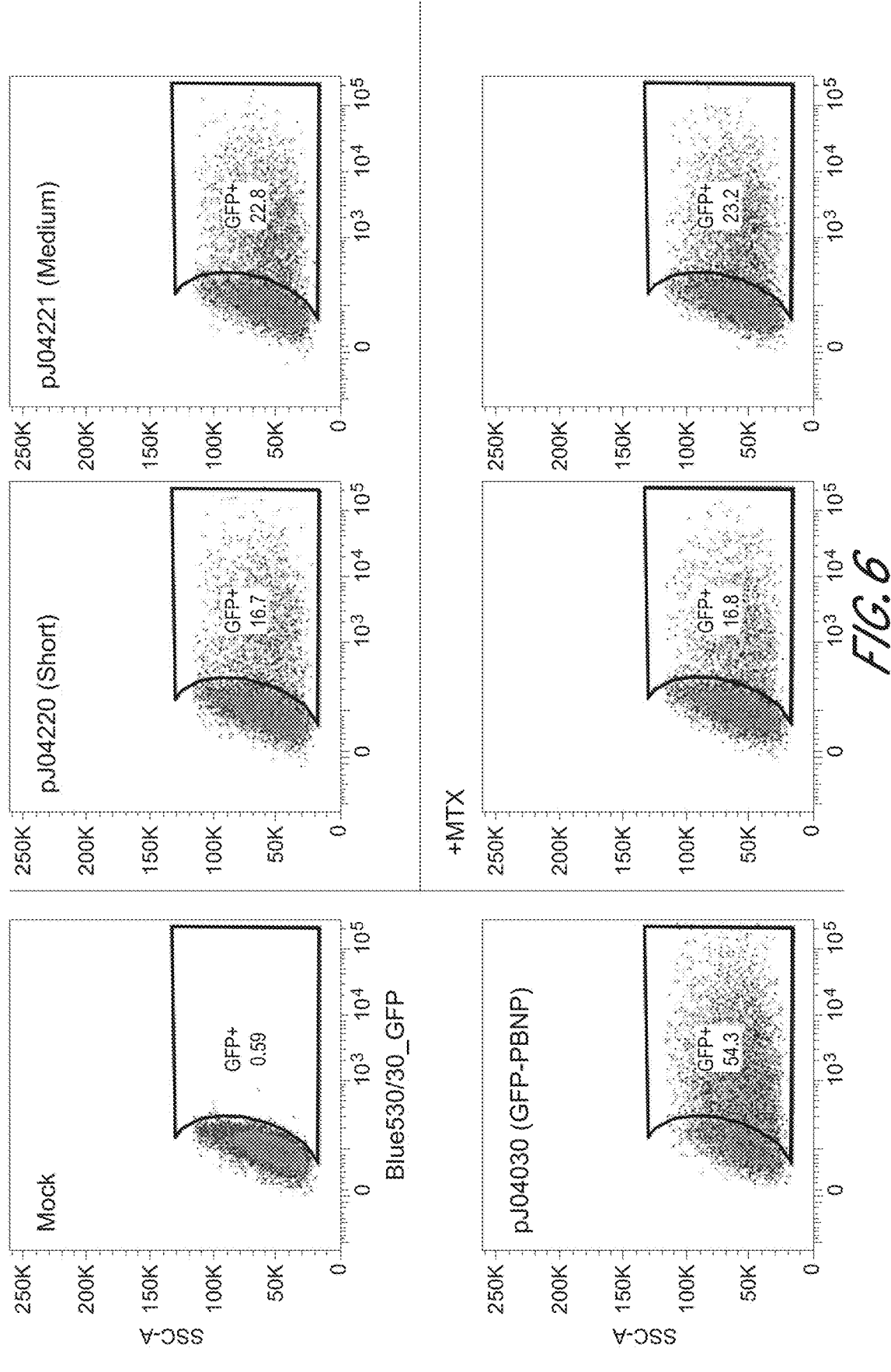
FIG. 6 shows experimental results of expression of GFP on day two for samples receiving DNA. On day two, expression of GFP is visible in all electroporated samples receiving DNA containing the gene of interest (including the control), indicating that the plasmid is functional and capable of utilizing cell machinery to promote expression of the gene of interest.
Figure 6:
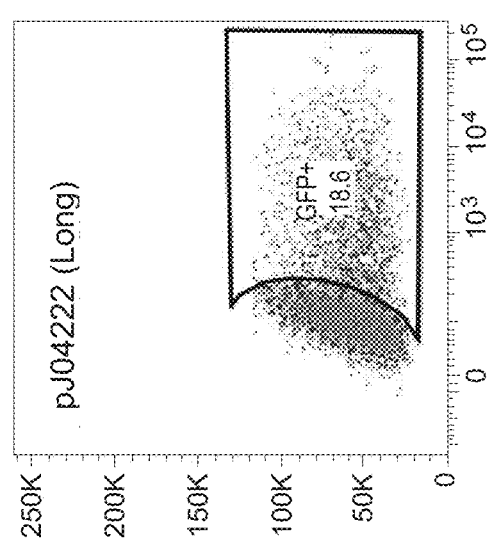
Figure 6:
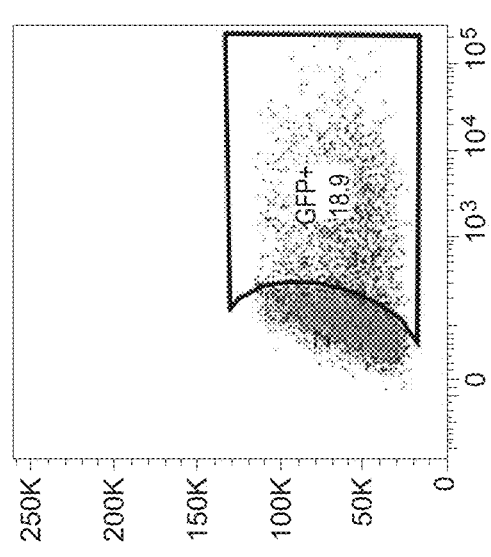

As shown in FIG. 6, on day two, expression of GFP is visible in all electroporated samples, which received DNA containing the GOT (including the control); this indicates the plasmid is functional and utilizes cell machinery to promote expression of the GOI.

Figure 7:
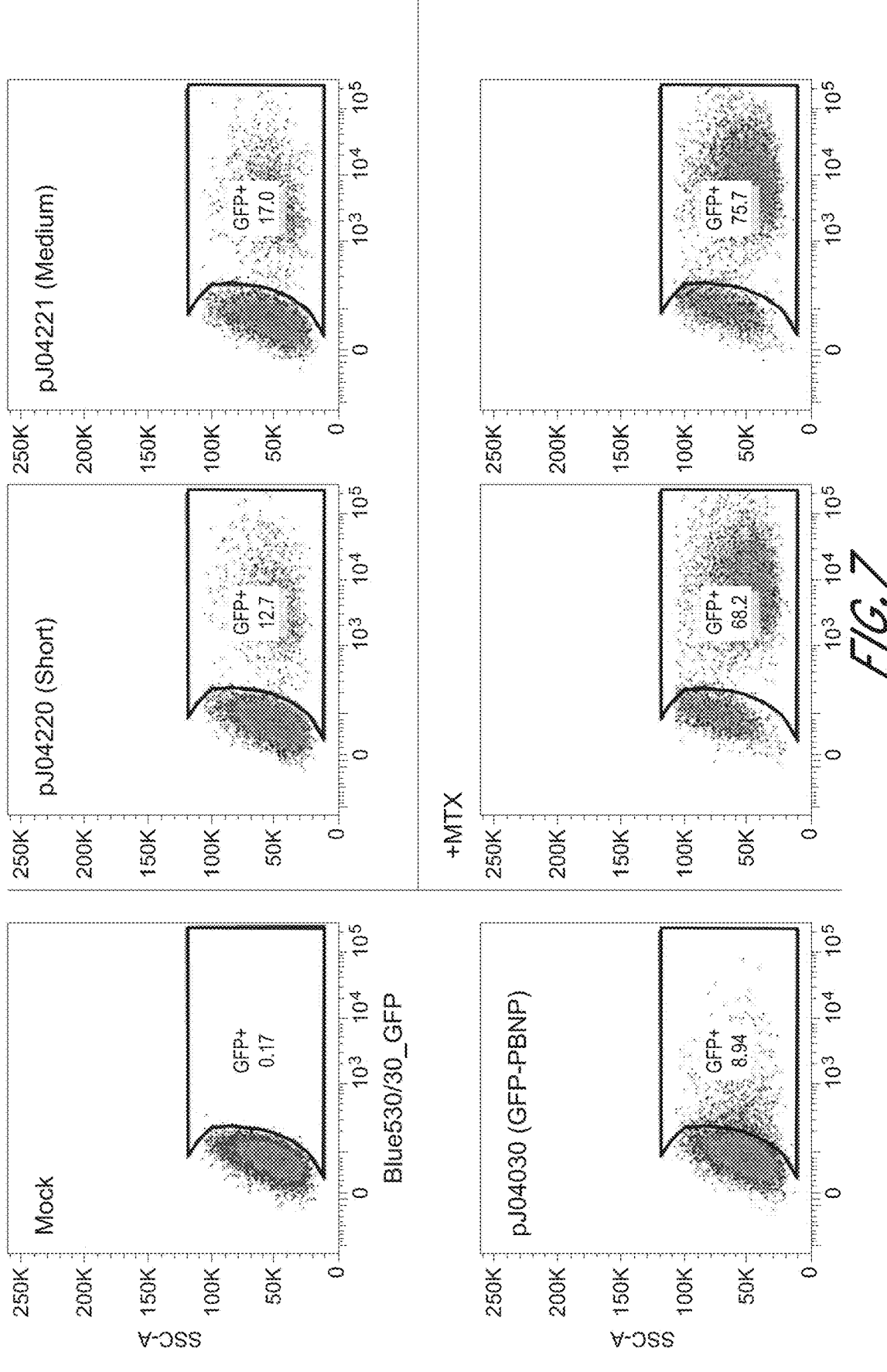
FIG. 7 shows experimental results of expression of GFP on day seven for samples receiving DNA. By day seven, the distinctiveness of the GFP-positive cell population is stronger in conditions subjected to drug selection, indicating that the selection is functional and capable of purifying against unintegrated populations.
Figure 7:
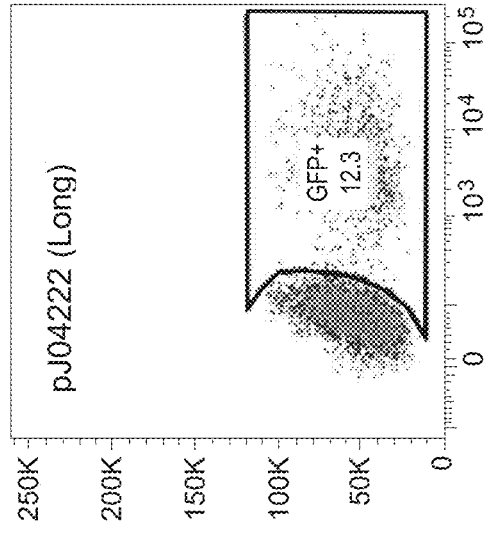
Figure 7:
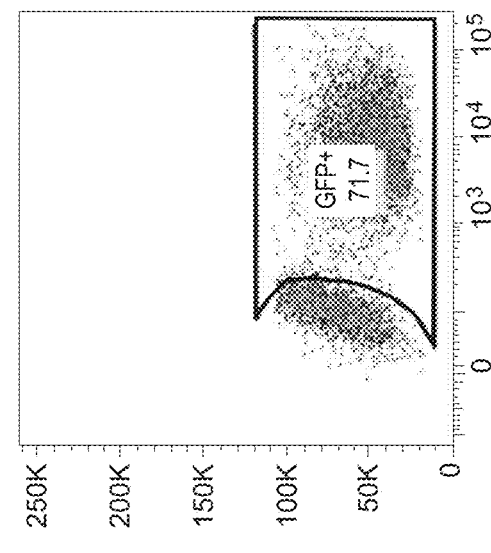

By day seven, as shown in FIG. 7, expression of GFP is still visible, and distinct populations of GFP-positive and GFP-negative cells are beginning to form (while the control-DNA condition has reduced expression); this indicates the intron is functional and activates the transposase, which is also functional and capable of integrating the GOT transposon. By day seven, the distinctiveness of the GFP-positive cell population is stronger in conditions subjected to drug selection; this indicates the selection is functional and capable of purifying against unintegrated populations.

Figure 8:
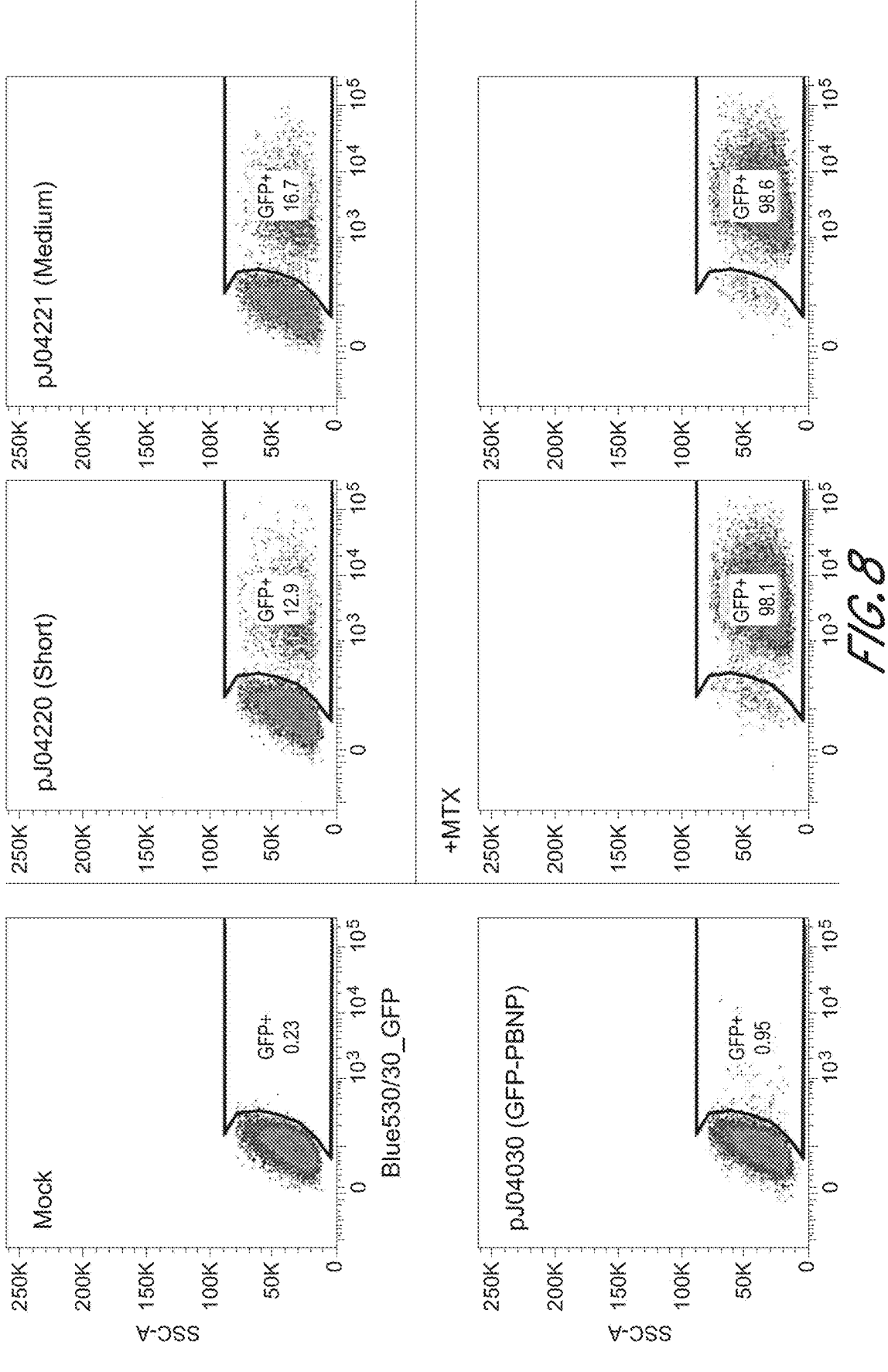
FIG. 8 shows experimental results of expression of GFP on day fourteen for samples receiving DNA. By day fourteen, the functionalities of the intron, transposase, and drug selection remain successful, producing near-pure populations of GFP-positive cells in drug-selected conditions. Transient expression of GFP is severely reduced in the control-DNA condition, indicating that the expression seen in the cell populations is not due to random integration, but rather transposase-directed integration.
Figure 8:
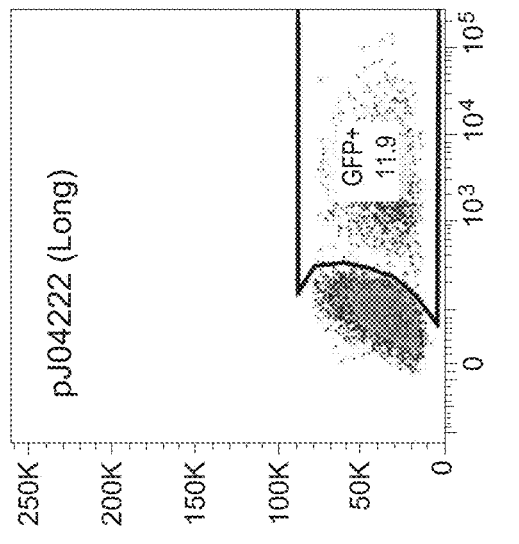
Figure 8:
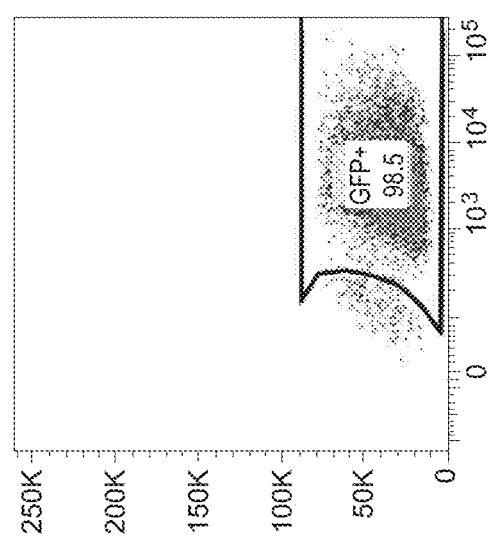

By day fourteen, as shown in FIG. 8, the functionalities of the intron, transposase, and drug selection continue to be successful, producing near-pure populations of GFP-posi-tive cells in drug-selected conditions. Meanwhile, transient expression of GFP is severely reduced in the control-DNA condition, indicating the expression seen in the above-mentioned populations is not due to random integration, but to transposase-directed integration.

Example 2: Self-Inactivating Transposase System for Primary Cells

Primary human T cells were electroporated on day three with a DNA construct at varying concentration, in various conditions containing a self-inactivating transposase and a gene of interest (GOI), FMC63scfv-IgG4-CD28-41BB-CD3zeta-P2A-DHFRdm-T2A-EGFRt in this example, within a transposon. Control conditions included a non-electroporated sample and a no-DNA electroporated sample (Mock). All cells were cultured in a GREX for ten days, with methotrexate-mediated drug selection (+MTX) against unin-tegrated cell populations beginning on day five. Expression of the GOI was observed over the course of ten days via flow cytometric analysis of EGFRt expression, and time points were taken on days five and ten. Flow cytometry was performed on all samples to compare expression levels across conditions, and gating was drawn against the Mock sample.

Plasmid functionality was confirmed via data collected on day five and ten. Intron and transposase functionalities were confirmed via data collected on days five and ten. Drug selection functionality was confirmed via data collected on days five and ten. Flow cytometry results are shown in FIGS. 9-10.

Figure 9:
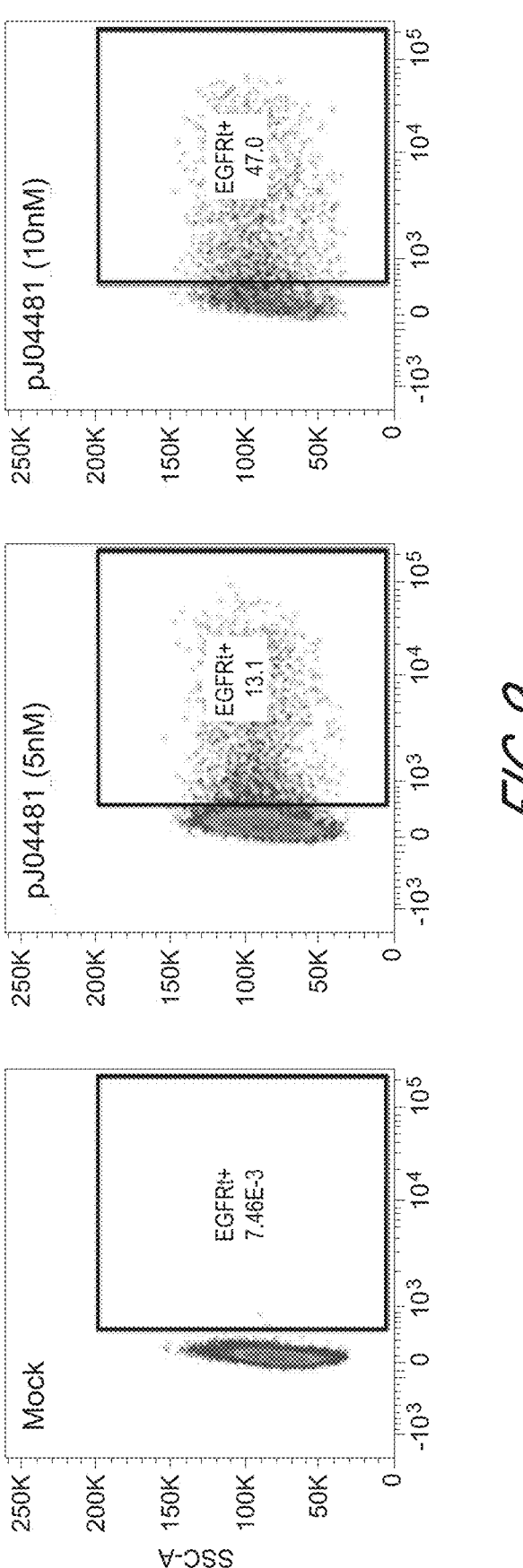
FIG. 9 shows experimental results of expression using flow cytometry of EGFRt on day five for samples receiving DNA at different concentrations. On day five, expression of EGFRt is visible in all electroporated samples receiving DNA containing the gene of interest, indicating that the plasmid is functional and capable of utilizing cell machinery to promote expression of the gene of interest.
Figure 9:
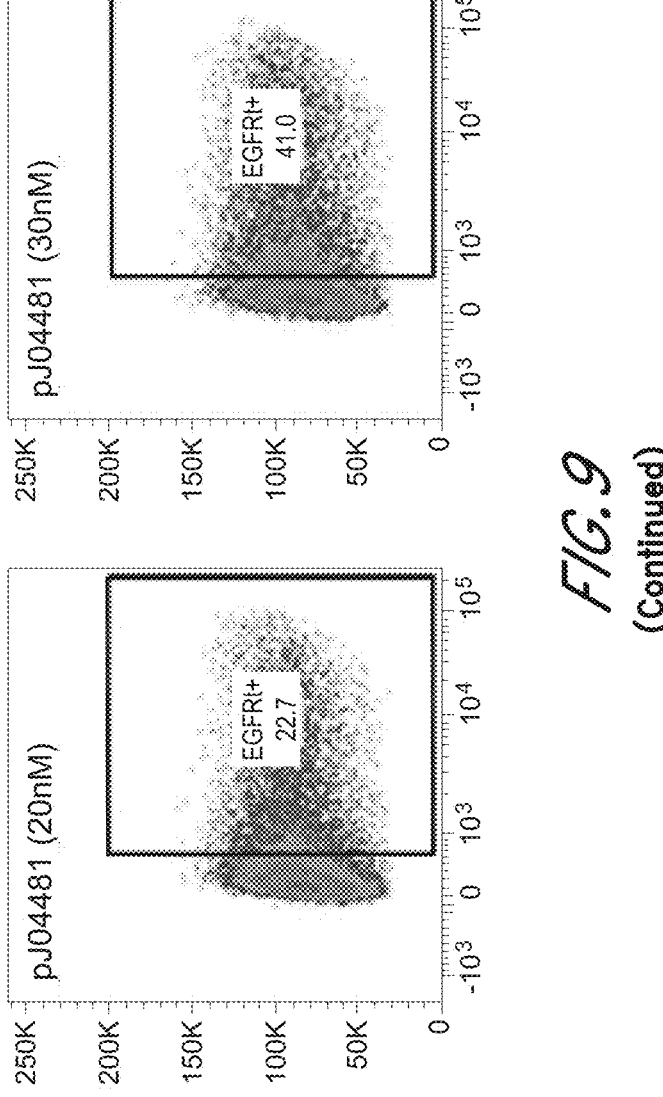

As shown in FIG. 9, on day five, analysis of expression by flow cytometry of EGFRt is visible in all electroporated samples that received DNA containing the GOI. This indicates the plasmid is functional and utilizes cell machinery to promote expression of the GOI.

Figure 10:
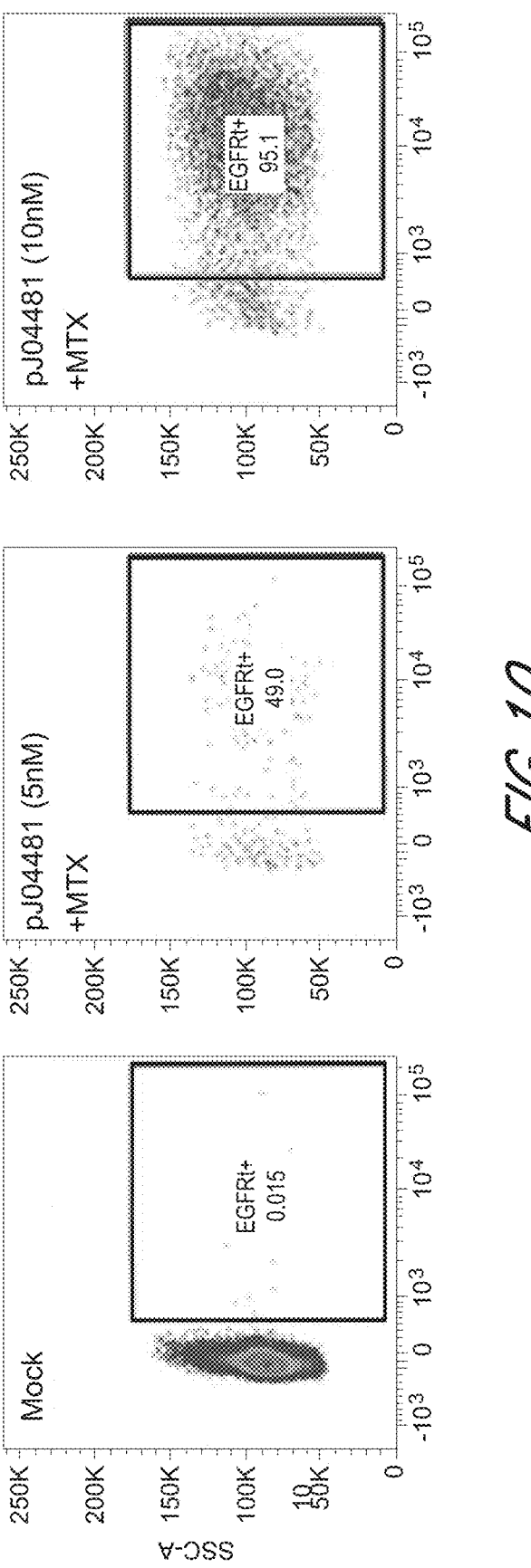
FIG. 10 shows experimental results using flow cytometry analyzing expression of EGFRt on day ten for samples receiving DNA at different concentrations and after undergoing drug selection by methotrexate (MTX). By day ten, the functionalities of the intron, transposase, and drug selection remain successful, producing near-pure populations of EGFRt-positive cells in drug-selected conditions.
Figure 10:
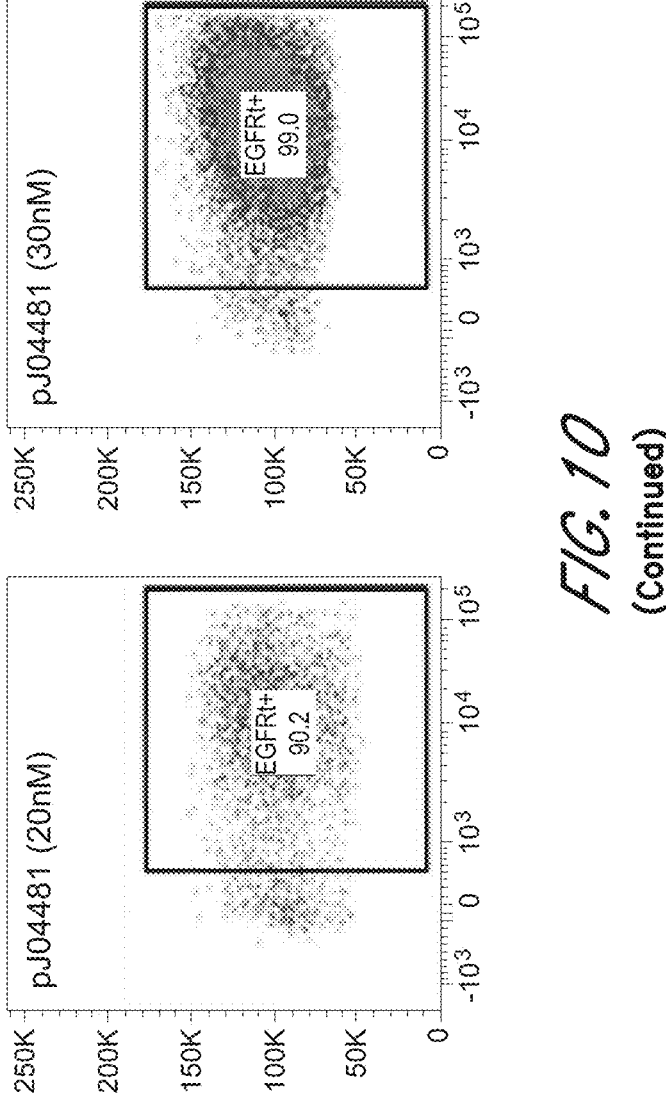

By day ten, as shown in FIG. 10, the functionalities of the intron, transposase, and drug selection continue to be successful in primary T-cells, producing near-pure populations of EGFRt-positive cells in drug-selected conditions as analyzed by flow cytometry. Accordingly, this second example demonstrates that the methods and procedures described herein allow for efficient integration of a desired gene into primary human cells such as T-cells and stem cells.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an"

limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

SEQUENCE LISTING
TRANSPOSASE REGION
PIGGYBAC TRANSPOSASE:
5' CATALYTIC REGION (SEQ ID NO: 1)
ATGGGCAGCAGCCTGGACGACGAGCACATCCTGTCTGCCCTGCTGCAATC

CGACGATGAGCTCGTGGGCGAGGACAGCGACAGCGAGATCAGCGATCACG

TGTCCGAGGACGACGTGCAGTCCGACACCGAGGAAGCCTTCATCGACGAG

GTGCACGAAGTGCAGCCTACCAGCAGCGGCTCCGAGATCCTGGACGAGCA

GAACGTGATCGAGCAGCCCGGAAGCTCCCTGGCCAGCAACAGAATCCTGA

CCCTGCCCCAGCGGACCATCCGGGGCAAGAACAAGCACTGCTGGTCCACC

AGCAAGAGCACCCGGCGGTCCAGAGTGTCCGCCCTGAATATCGTGCGGAG

CCAGAGGGGCCCCACCCGGATGTGCAGAAACATCTACGACCCCCTGCTGT

GCTTCAAGCTGTTCTTCACCGACGAGATCATCTCTGAGATCGTGAAGTGG

ACCAACGCCGAGATCTCCCTGAAGCGGCGCGAGTCTATGACCGGCGCCAC

CTTCAGAGACACCAACGAGGACGAGATCTACGCCTTCTTCGGCATCCTCG

TGATGACCGCCGTGCGGAAGGACAACCACATGAGCACCGACGACCTGTTC

-continued

GACCGGTCCCTGAGCATGGTGTACGTGTCCGTGATGAGCCGGGACAGATT

CGACTTCCTGATCCGGTGCCTGCGGATGGACGACAAGAGCATCAGACCCA

CCCTGCGCGAGAACGACGTGTTCACCCCTGTGCGGAAGATCTGGGACCTG

TTCATCCACCAGTGCATCCAGAACTACACCCCTGGCGCCCACCTGACCAT

CGACGAACAGCTGCTGGGCTTCAGAGGCCGGTGCCCCTTCAGAATGTACA

TCCCCAACAAGCCCTCTAAGTACGGCATCAAGATCCTGATGATGTGCGAC

AGCGGCACCAAGTACATGATCAACGGCATGCCCTACCTGGGCAGAGGCAC

CCAGACAAATGGCGTGCCACTGGGCGAGTACTACGTGAAAGAACTGAGCA

AGCCTGTGCACGGCTCCTGCCGGAACATCACCTGTGACAACTGGTTCACC

TCCATCCCCCTGGCCAAGAATCTGCTGCAGGAACCCTACAAGCTGACAAT

CGTGGGCACCGTGCGGTCCAACAAGCGCGAGATTCCCGAG

EF1a INTRON (SEQ ID NO: 2)
GTAAGTGCCGTGTGTGGTTCCCGCGGGCCTGGCCTCTTTACGGGTTATGG

CCCTTGCGTGCCTTGAATTACTTCCACGCCCCTGGCTGCAGTACGTGATT

CTTGATCCCGAGCTTCGGGTTGGAAGTGGGTGGGAGAGTTCGAGGCCTTG

CGCTTAAGGAGCCCCTTCGCCTCGTGCTTGAGTTGAGGCCTGGCTTGGGC

GCTGGGGCCGCCGCGTGCGAATCTGGTGGCACCTTCGCGCCTGTCTCGCT

GCTTTCGATAAGTCTCTAGCCATTTAAAATTTTTGATGACCTGCTGCGAC

GCTTTTTTTCTGGCAAGATAGTCTTGTAAATGCGGGCCAAGATCTGCACA

CTGGTATTTCGGTTTTTGGGGCCGCGGGCGGCGACGGGGCCCGTGCGTCC

CAGCGCACATGTTCGGCGAGGCGGGGCCTGCGAGCGCGGCCACCGAGAAT

CGGACGGGGGTAGTCTCAAGCTGGCCGGCCTGCTCTGGTGCCTGGCCTCG

CGCCGCCGTGTATCGCCCCGCCCTGGGCGGCAAGGCTGGCCCGGTCGGCA

CCAGTTGCGTGAGCGGAAAGATGGCCGCTTCCCGGCCCTGCTGCAGGGAG

CTCAAAATGGAGGACGCGGCGCTCGGGAGAGCGGGCGGGTGAGTCACCCA

CACAAAGGAAAAGGGCCTTTCCGTCCTCAGCCGTCGCTTCATGTGACTCC

ACGGAGTACCGGGCGCCGTCCAGGCACCTCGATTAGTTCGCTTTTGGAGT

ACGTCGTCTTTAGGTTGGGGGGAGGGGTTTTATGCGATGGAGTTTCCCCA

CACTGAGTGGGTGGAGACTGAAGTTAGGCCAGCTTGGCACTTGATGTAAT

TCTCCTTGGAATTTGCCCTTTTTGAGTTTGGATCTTGGTTCATTCTCAAG

CCTCAGACAGTGGTTCAAAGTTTTTTTCTTCCATTTCAG

PIGGYBAC TRANSPOSASE:
5' CATALYTIC REGION + STOP CODON (SEQ ID NO: 3)
GTGCTGAAGAACTCCCGGTCCAGACCTGTGGGCACCAGCATGTTCTGCTT

CGACGGCCCTCTGACCCTGGTGTCCTACAAGCCCAAGCCCGCCAAGATGG

TGTACCTGCTGAGCAGCTGTGACGAGGACGCCAGCATCAACGAGAGCACC

GGCAAGCCCCAGATGGTCATGTACTACAACCAGACCAAGGGCGGCGTGGA

CACCCTGGACCAGATGTGCAGCGTGATGACATGCAGCAGAAAGACCAACC

GGTGGCCCATGGCCCTGCTGTACGGCATGATCAATATCGCCTGCATCAAC

AGCTTCATCATCTACTCCCACAACGTGTCCAGCAAGGGCGAGAAGGTGCA

GAGCCGGAAGAAATTCATGCGGAACCTGTACATGAGCCTGACCTCCAGCT

-continued

TCATGAGAAAGCGGCTGGAAGCCCCCACCCTGAAGAGATACCTGCGGGAC

AACATCAGCAACATCCTGCCCAACGAGGTGCCCGGCACCAGCGACGATAG

CACAGAGGAACCCGTGATGAAGAAGCGGACCTACTGCACCTACTGTCCCT

CTAAAATCCGGCGGAAGGCCAACGCCAGCTGCAAAAAGTGCAAGAAAGTG

ATCTGCCGCGAGCACAACATCGATATGTGCCAGAGCTGCTTCTGA

SV40 LATE POLY(A)
                              (SEQ ID NO: 4)
GCTTTATTTGTGAAATTTGTGATGCTATTGCTTTATTTGTAACCATTATA

AGCTGCAATAAACAAGTTAACAACAACAATTGCATTCATTTTATGTTTCA

GGTTCAGGGGGAGATGTGGGAGGTTTTTTAAAGC

TRANSPOSON REGION:
5' TERMINAL REPEAT
                              (SEQ ID NO: 5)
TTAACCCTAGAAAGATAATCATATTGTGACGTACGTTAAAGATAATCATG

CGTAAAATTGACGCATGTGTTTTATCGGTCTGTATATCGAGGTTTATTTA

TTAATTTGAATAGATATTAAGTTTTATTATATTTACACTTACATACTAAT

AATAAATTCAACAAACAATTTATTTATGTTTATTTATTTATTAAAAAAAA

ACAAAAACTCAAAATTTCTTCTATAAAGTAACAAAACTTTTA

CORE/INSULATOR
                              (SEQ ID NO: 6)
GAGGGACAGCCCCCCCCCAAAGCCCCCAGGGATGTAATTACGTCCCTCCC

CCGCTAGGGGGCAGCAGCGAGCCGCCCGGGGCTCCGCTCCGGTCCGGCGC

TCCCCCCGCATCCCCGAGCCGGCAGCGTGCGGGGACAGCCCGGGCACGGG

GAAGGTGGCACGGGATCGCTTTCCTCTGAACGCTTCTCGCTGCTCTTTGA

GCCTGCAGACACCTGGGGGGATACGGGGAAAAGGCTCGCGA

EF1a PROMOTER
                              (SEQ ID NO: 7)
GGATCTGCGATCGCTCCGGTGCCCGTCAGTGGGCAGAGCGCACATCGCCC

ACAGTCCCCGAGAAGTTGGGGGGAGGGGTCGGCAATTGAACCGGTGCCTA

GAGAAGGTGGCGCGGGGTAAACTGGGAAAGTGATGTCGTGTACTGGCTCC

GCCTTTTTCCCGAGGGTGGGGGAGAACCGTATATAAGTGCAGTAGTCGCC

GTGAACGTTCTTTTTCGCAACGGGTTTGCCGCCAGAACACAGCTG eGFP Flanked by enzymatic cut sites NheI and BamHI
                              (SEQ ID NO: 8)
GCTAGCATGCCCGCCATGAAGATCGAGTGCCGCATCACCGGCACCCTGAA

CGGCGTGGAGTTCGAGCTGGTGGGCGGCGGAGAGGGCACCCCCGAGCAGG

GCCGCATGACCAACAAGATGAAGAGCACCAAAGGCGCCCTGACCTTCAGC

CCCTACCTGCTGAGCCACGTGATGGGCTACGGCTTCTACCACTTCGGCAC

CTACCCCAGCGGCTACGAGAACCCCTTCCTGCACGCCATCAACAACGGCG

GCTACACCAACACCCGCATCGAGAAGTACGAGGACGGCGGCGTGCTGCAC

GTGAGCTTCAGCTACCGCTACGAGGCCGGCCGCGTGATCGGCGACTTCAA

GGTGGTGGGCACCGGCTTCCCCGAGGACAGCGTGATCTTCACCGACAAGA

TCATCCGCAGCAACGCCACCGTGGAGCACCTGCACCCCATGGGCGATAAC

GTGCTGGTGGGCAGCTTCGCCCGCACCTTCAGCCTGCGCGACGGCGGCTA

CTACAGCTTCGTGGTGGACAGCCACATGCACTTCAAGAGCGCCATCCACC

CCAGCATCCTGCAGAACGGGGGCCCCATGTTCGCCTTCCGCCGCGTGGAG

-continued

GAGCTGCACAGCAACACCGAGCTGGGCATCGTGGAGTACCAGCACGCCTT

CAAGACCCCCATCGCCTTCGCCGGATCC

T2A with AGG ta2
                              (SEQ ID NO: 9)
GGCGGCGGAGAGGGCAGAGGAAGTCTTCTAACATGCGGTGACGTGGAGGA

GAATCCCGGCCCTAGG

DHFRdm + STOP CODON Followed by enzymatic cut
sites Acc65I and Not I
                              (SEQ ID NO: 10)
ATGGTTGGTTCGCTAAACTGCATCGTCGCTGTGTCCCAGAACATGGGCAT

CGGCAAGAACGGGGACTTCCCCTGGCCACCGCTCAGGAATGAATCCAGAT

ATTTCCAGAGAATGACCACAACCTCTTCAGTAGAAGGTAAACAGAATCTG

GTGATTATGGGTAAGAAGACCTGGTTCTCCATTCCTGAGAAGAATCGACC

TTTAAAGGGTAGAATTAATTTAGTTCTCAGCAGAGAACTCAAGGAACCTC

CACAAGGAGCTCATTTTCTTTCCAGAAGTCTAGATGATGCCTTAAAACTT

ACTGAACAACCAGAATTAGCAAATAAAGTAGACATGGTCTGGATAGTTGG

TGGCAGTTCTGTTTATAAGGAAGCCATGAATCACCCAGGCCATCTTAAAC

TATTTGTGACAAGGATCATGCAAGACTTTGAAAGTGACACGTTTTTTCCA

GAAATTGATTTGGAGAAATATAAACTTCTGCCAGAATACCCAGGTGTTCT

CTCTGATGTCCAGGAGGAGAAAGGCATTAAGTACAAATTTGAAGTATATG

AGAAGAATGATTAAGGTACCGCGGCCGC

RBG/POLY(A)
                              (SEQ ID NO: 11)
TTTTCCCTCTGCCAAAAATTATGGGGACATCATGAAGCCCCTTGAGCATC

TGACTTCTGGCTAATAAAGGAAATTTATTTTCATTGCAATAGTGTGTTGG

AATTTTTTGTGTCTCTCACTCGGAAGGACATAAGG

CORE/INSULATOR
                              (SEQ ID NO: 12)
ATGGCTAGATCTTTTTCCCCGTATCCCCCCAGGTGTCTGCAGGCTCAAAG

AGCAGCGAGAAGCGTTCAGAGGAAAGCGATCCCGTGCCACCTTCCCCGTG

CCCGGGCTGTCCCCGCACGCTGCCGGCTCGGGGATGCGGGGGGAGCGCCG

GACCGGAGCGGAGCCCCGGGCGGCTCGCTGCTGCCCCCCTAGCGGGGGAGG

GACGTAATTACATCCCTGGGGGCTTTGGGGGGGGGCTGTCCCT

3' TERMINAL REPEAT
                              (SEQ ID NO: 13)
GATATCTATAACAAGAAAATATATATATAATAAGTTATCACGTAAGTAGA

ACATGAAATAACAATATAATTATCGTATGAGTTAAATCTTAAAAGTCACG

TAAAAGATAATCATGCGTCATTTTGACTCACGCGGTCGTTATAGTTCAAA

ATCAGTGACACTTACCGCATTGACAAGCACGCCTCACGGGAGCTCCAAGC

GGCGACTGAGATGTCCTAAATGCACAGCGACGGATTCGCGCTATTTAGAA

AGAGAGAGCAATATTTCAAGAATGCATGCGTCAATTTTACGCAGACTATC

TTTCTAGGGTTAA

-continued                                            -continued

NANOPLASMBD BACKBONE:
TRPA TERMINATOR Preceded by enzymatic cut site
SalI (SEQ ID NO: 14)
GTCGACCCGCCTAATGAGCCGCCTAATGAGCGGGCTTTTTTTT

R6K MINI ORIGIN (SEQ ID NO: 15)
GGCTTGTTGTCCACAACCGTTAAACCTTAAAAGCTTTAAAAGCCTTATAT

ATTCTTTTTTTTCTTATAAAACTTAAAACCTTAGAGGCTATTTAAGTTGC

TGATTTATATTAATTTTATTGTTCAAACATGAGAGCTTAGTACGTGAAAC

ATGAGAGCTTAGTACGTTAGCCATGAGAGCTTAGTACGTTAGCCATGAGG

GTTTAGTTCGTTAAACATGAGAGCTTAGTACGTTAAACATGAGAGCTTAG

TACGTACTATCAACAGGTTGAACTGCTGATC

RNA-OUT (SEQ ID NO: 16)
CACGTTGTGGTAGAATTGGTAAAGAGAGTCGTGTAAAATATCGAGTTCGC

ACATCTTGTTGTCTGATTATTGATTTTTGGCGAAACCATTTGATCATATG

ACAAGATGTGTATCTACCTTAACTTAATGATTTTGATAAAAATCATTAGG

CMV-ENHANCER (SEQ ID NO: 17)
CTAGTTATTAATAGTAATCAATTACGGGGTCATTAGTTCATAGCCCATAT

ATGGAGTTCCGCGTTACATAACTTACGGTAAATGGCCCGCCTGGCTGACC

GCCCAACGACCCCCGCCCATTGACGTCAATAATGACGTATGTTCCCATAG

TAACGCCAATAGGGACTTTCCATTGACGTCAATGGGTGGAGTATTTACGG

TAAACTGCCCACTTGGCAGTACATCAAGTGTATCATATGCCAAGTACGCC

CCCTATTGACGTCAATGACGGTAAATGGCCCGCCTGGCATTATGCCCAGT

ACATGACCTTATGGGACTTTCCTACTTGGCAGTACATCTACGTATTAGTC

ATCGCTATTACCATGGTGATGCGGTTTTGGCAGTACATCAATGGGCGTGG

ATAGCGGTTTGACTCACGGGGATTTCCAAGTCTCCACCCCATTGACGTCA

ATGGGAGTTTGTTTTGG

CMV-CORE PROMOTER (SEQ ID NO: 18)
CACCAAAATCAACGGGACTTTCCAAAATGTCGTAACAACTCCGCCCCATT

GACGCAAATGGGCGGTAGGCGTGTACGGTGGGAGGTCTATATAAGCAGAG

CTCGTTTAGTGAACCGTCAGATCGCCTGGAGACGCCATCCACGCTGTTTT

GACCTCCATAGAA

SUICIDE GENE:
SR39TK (SEQ ID NO: 19)
ATGCCCACGCTACTGCGGGTTTATATAGACGGTCCCCACGGGATGGGGAA

AACCACCACCACGCAACTGCTGGTGGCCCTGGGTTCGCGCGACGATATCG

TCTACGTACCCGAGCCGATGACTTACTGGCGGGTGCTGGGGGCTTCCGAG

ACAATCGCGAACATCTACACCACACAACACCGCCTCGACCAGGGTGAGAT

ATCGGCCGGGGACGCGGCGGTGGTAATGACAAGCGCCCAGATAACAATGG

GCATGCCTTATGCCGTGACCGACGCCGTTCTGGCTCCTCATATCGGGGGG

GAGGCTGGGAGCTCACATGCCCCGCCCCCGGCCCTCACCATCTTCCTCGA

CCGCCATCCCATCGCCTTCATGCTGTGCTACCCGGCCGCGCGGTACCTTA

TGGGCAGCATGACCCCCCAGGCCGTGCTGGCGTTCGTGGCCCTCATCCCG

CCGACCTTGCCCGGCACCAACATCGTGCTTGGGGCCCTTCCGGAGGACAG

ACACATCGACCGCCTGGCCAAACGCCAGCGCCCCGGCGAGCGGCTGGACC

TGGCTATGCTGGCTGCGATTCGCCGCGTTTACGGGCTACTTGCCAATACG

GTGCGGTATCTGCAGTGCGGCGGGGTCGTGGCGGGAGGACTGGGGACAGCT

TTCGGGGACGGCCGTGCCGCCCCAGGGTGCCGAGCCCCAGAGCAACGCGG

GCCCACGACCCCATATCGGGGACACGTTATTTACCCTGTTTCGGGCCCCC

GAGTTGCTGGCCCCCAACGGCGACCTGTATAACGTGTTTGCCTGGGCCTT

GGACGTCTTGGCCAAACGCCTCCGTTCCATGCACGTCTTTATCCTGGATT

ACGACCAATCGCCCGCCGGCTGCCGGGACGCCCTGCTGCAACTTACCTCC

GGGATGGTCCAGACCCACGTCACCACCCCCGGCTCCATACCGACGATATG

CGACCTGGCGCGCACGTTTGCCCGGGAGATGGGGGAGGCTAAC

T2A (SEQ ID NO: 20)
GGCGGCGGAGAGGGCAGAGGAAGTCTTCTAACATGCGGTGACGTGGAGGA

GAATCCCGGCCCT

---

What is claimed is:

1. A vector for delivery of a payload into a cell genome, the vector comprising (a), (b), and (c) in a 5' to 3' order:

(a) a first nucleic acid comprising (i) a nucleotide sequence encoding a transposase, and (ii) an intron comprising a first transposase recognition site (TRS), wherein the intron is inserted into the nucleotide sequence encoding the transposase;

(b) a second nucleic acid encoding the payload; and (c) a second TRS.

2. The vector of claim 1, wherein the vector is a circular vector.

3. The vector of claim 1, wherein the transposase is a Tn5 transposase, a MuA transposase, a Tn552 transposase, or a mariner transposase.

4. The vector of claim 1, wherein the transposase is encoded by a sequence having at least 90% sequence identity to the nucleotide sequence of SEQ ID NO:01 or SEQ ID NO:03.

5. The vector of claim 1, wherein the intron is derived from a nucleic acid lacking the first TRS and, wherein the nucleic acid lacking the first TRS comprises a sequence having at least 90% sequence identity to the nucleotide sequence of SEQ ID NO:02.

6. The vector of claim 1, wherein the first TRS and the second TRS are both derived from a transposon selected from a Tn5 transposon, a MuA transposon, a Tn552 transposon, or a mariner transposon.

7. The vector of claim 1, wherein the first TRS and the second TRS comprise a sequence having at least 90% sequence identity to the nucleotide sequence of SEQ ID NO:05 or SEQ ID NO:13.

8. The vector of claim 1, wherein the payload encodes a therapeutic protein.

9. The vector of claim 1, further comprising a first promoter operably linked to the first nucleic acid.

10. The vector of claim 1, further comprising a selectable marker.

11. The vector of claim 10, wherein the selectable marker encodes a dihydrofolate reductase (DHFR).

12. The vector of claim 1, further comprising a nucleic acid encoding a first polyA signal operably linked to the second nucleic acid, or a second polyA signal operably linked to the third nucleic acid.

13. A cell comprising the vector of claim 1.

14. The cell of claim 13, wherein the cell is a mammalian cell.

15. The cell of claim 14, wherein the cell is a human cell.

* * * * *